United States Patent [19]

Hurwitz et al.

[11] 4,312,229

[45] Jan. 26, 1982

[54] DETECTION, CHARACTERIZATION, AND STUDY OF FLAWS IN WORK WITH ACOUSTIC ENERGY

[75] Inventors: Michael J. Hurwitz, Pittsburgh, Pa.; Paul G. Kennedy, Linthicum Heights, Md.; James W. H. Justice, Murrysville, Pa.

[73] Assignee: Westinghouse Electric Corp., Pittsburgh, Pa.

[21] Appl. No.: 32,841

[22] Filed: Apr. 24, 1979

[51] Int. Cl.$^3$ ............................................. G01N 29/04
[52] U.S. Cl. ......................................... 73/603; 73/620
[58] Field of Search ................. 73/603, 620, 625, 626, 73/634; 128/660

[56] References Cited

U.S. PATENT DOCUMENTS

| | | | |
|---|---|---|---|
| 4,026,144 | 5/1977 | Gericke et al. | 73/603 |
| 4,058,001 | 11/1977 | Waxman | 73/620 |
| 4,137,775 | 2/1979 | LeMay | 73/620 |
| 4,137,777 | 2/1979 | Haverl et al. | 73/620 |

Primary Examiner—Anthony V. Ciarlante
Attorney, Agent, or Firm—Daniel C. Abeles

[57] ABSTRACT

The work is scanned by acoustic energy from a focused-arc transducer and from an acoustic-lens transducer. An echo-ranging subassembly energizes the focused-arc transducer and processes the echo trains relfected from the lines or pencils in the work along which the acoustic energy is focused. A holographic echo-processing subassembly is connected to energize the acoustic-lens transducer and to process the echoes reflected from the work where the energy from the acoustic lens impinges. The echo-ranging subassembly and the holographic echo-processing subassembly are enabled alternately and the acoustic energy from the focused-arc transducer and from the acoustic-lens transducer impinge on, and is reflected by, each of a succession of elemental areas of the work. The outputs of the echo-ranging subassembly and of the holographic echo-processing subassembly are supplied to an elastic store which may include one or more shift registers. The elastic store stores a set of magnitudes corresponding to the components of each echo train resulting from the impingement on each elemental area of acoustic energy from the focused-arc transducer and to the echo or echoes resulting from the impingement at a predetermined depth in the work of acoustic energy from the acoustic-lens transducer. The content of the elastic store is transferred to a video disc, the intelligence for each strip or each line of the work which is scanned is recorded on a track of the disc. A cathode-ray tube display is produced from the intelligences stored in the disc for the trains of echo components reflected from each strip of the work and a hologram is produced of the intelligences stored in the disc for the trains of echo components reflected from each strip of the work and a hologram is produced of the intelligences stored on the disc for the echoes resulting from the acoustic energy derived from the acoustic-lens transducer.

15 Claims, 28 Drawing Figures

POSITION OF VIDEO
LINES ON DISC
(TRACK 1)

POSITION OF VIDEO RASTER
LINES ON DISPLAY

RELATIVE POSITIONS OF "I"TH ELEMENTS ON DISC.

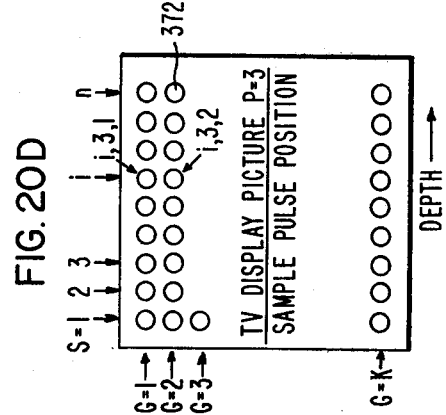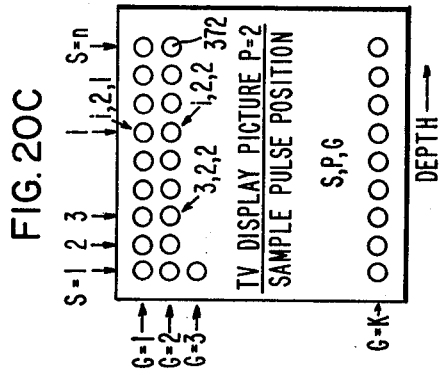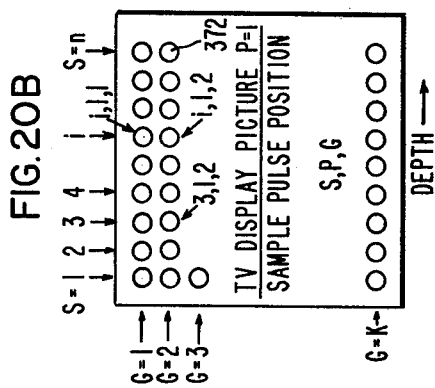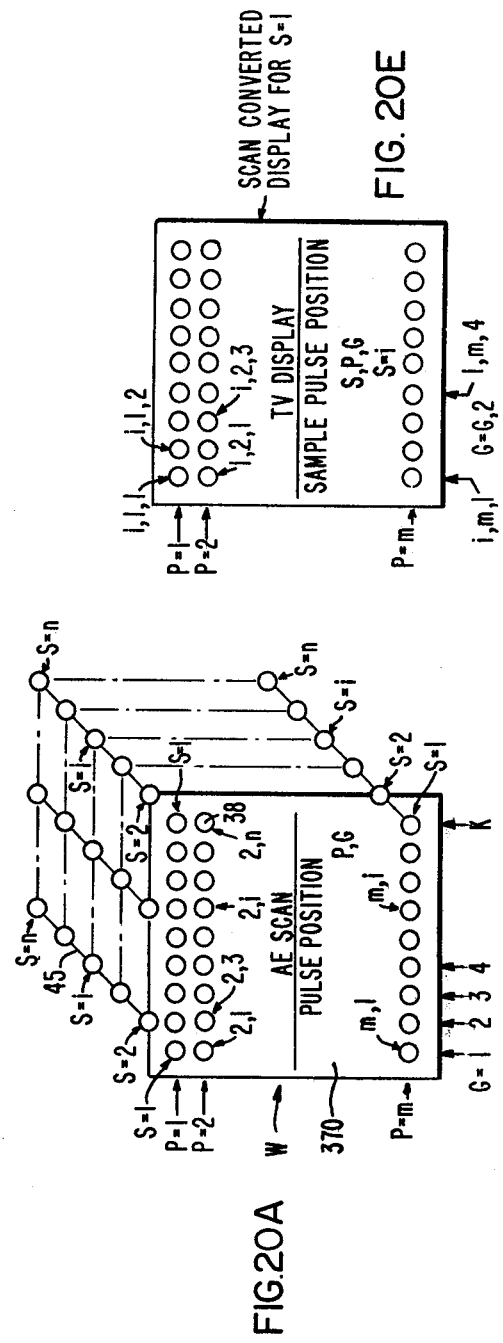

DETECTION, CHARACTERIZATION, AND STUDY OF FLAWS IN WORK WITH ACOUSTIC ENERGY

REFERENCE TO RELATED DOCUMENTS

This application relates to, and incorporates by reference, application Ser. No. 961,787 filed Nov. 17, 1978 to Michael J. Hurwitz for DETECTION, CHARACTERIZATION AND STUDY IN WORK OF FLAWS and an application Ser. No. 961,788 filed Nov. 17, 1978 to Michael J. Hurwitz for FLAW DETECTIONS CHARACTERIZATION AND STUDY. Both applications are assigned to Westinghouse Electric Corporation.

BACKGROUND OF THE INVENTION

This invention relates to the detection, characterization and study of flaws in work such as the walls of pressure vessels for nuclear reactors by means of acoustic energy. It has particular relationship to the display of the echo pattern from the work resulting from the reflection of acoustic energy impinging on the work. Application Ser. No. 961,788 (herein called Hurwitz application) discloses flaw detection, characterization and study in which a focused-arc transducer and a point-focusing transducer scan the work. The focused-arc transducer derives its energy from an echo-ranging subassembly. This subassembly also processes the echo trains resulting from the acoustic energy transmitted through the work producing a display which may be viewed to detect flaws. The point-focusing transducer derives the acoustic energy which it transmits to the work from a holographic echo-processing subassembly which also processes the resulting echoes received from the work. This subassembly produces a hologram which can be reconstructed into a recognizable optical image which can be viewed to detect, characterize or study flaws. It is desirable to provide, in connection with this or like apparatus, a readily operable, highly flexible method for displaying in detail and from different aspects the echo-imaged patterns produced by such apparatus. It is an object of this invention to provide such a method. It is also an object of this invention to provide, for the practice of such a method, facilities which can be readily and economically made available.

SUMMARY OF THE INVENTION

There is provided for the practice of this invention a display system including an elastic store and video record. Typically, the elastic store may be one or more shift registers, and the video record a video disc. Acoustic-echo intelligence as fed into, and stored in, the elastic store as it is produced and is then impressed on the disc. The content of the disc is displayed on a cathode-ray tube, CRT, or TV tube, and this display is observed and evaluated to detect, characterize, and study flaws. In this application the display apparatus will be referred to as a CRT.

Typically, the echo intelligence is derived from apparatus including a focused-arc transducer and a point-focusing transducer which are actuated by a scanner to scan the work elemental area by elemental area and to propagate acoustic energy to the work at each elemental area. The focused-arc transducer is connected typically to an echo-ranging subassembly which energizes this transducer and processes the resulting echo pattern reflected by the work. The point-focusing transducer is similarly cooperatively connected to a holographic echo-processing subassembly. The echo-ranging and holographic echo-processing subassembly are typically enabled alternately to propagate acoustic energy to successive elemental areas of the work. The echo intelligence from each of these elemental areas is stored as it is produced in the elastic store. Typically, the intelligence stored in the elastic store for each scanned setup of the work is transferred to a track of the video disc. Each track of the disc is displayed as a complete display or picture on the CRT. A number of CRT displays is thus available for the work subjected to flaw investigation. The CRT may be a television viewer tube.

The elastic store receives the intelligence as it is provided. Typically the apparatus disclosed in Hurwitz application or like apparatus includes a mechanical scanner which scans at a rate which is very small compared to the rate necessary to produce a CRT or TV display of the scanning directly. The scanning rate may also be variable. The elastic store records the echoes derived from the scanning at whatever rate it is produced. The intelligence stored in the elastic store is then recorded on a video record in a form such that a CRT display of the intelligence may be produced.

During each cycle of acoustic energy transmissions and resulting echo reception of the apparatus, acoustic energy is transmitted first with the focused-arc transducer and then with the point-focusing transducer or vice versa. To simplify the following discussion, it will be assumed that during each cycle the propagation is first from the focused-arc transducer and then from the point-focusing transducer. The scanner may be moved discontinuously over the elemental areas and stopped at each area long enough to afford time for propagation of acoustic energy by both transducers and reception of the resulting echoes. Or the scanning may be continuous and the relatively small movement between the propagation by the focused-arc transducer and reception of the resulting echo and the propagation by the point-focusing transducer and the reception of this resulting echo may be ignored. Or the point-focusing transducer may be offset slightly with respect to the focused-arc transducer so that it propagates acoustic energy to the same elemental area as the focused-arc transducer.

Once the intelligence is recorded on a video disc as disclosed above, further information may be derived by recording selected elements of each track on the above-described disc on an available track of the disc, or on a second disc. Typically, the selected element of each track may correspond to an elemental area of the work. The record on this available track (or on the second disc) can be reproduced on a CRT to show the echo pattern for sections through the work at right angle, or at any angle to the echo patterns shown by the initially recorded tracks of the disc. The elements of the tracks selected from the disc may also be those corresponding to the echoes resulting from the point-focusing transducer which are processed by the holographic echo-processing subassembly. This intelligence on the available track may be converted into a hologram which may be reconstructed into a visual optical image.

BRIEF DESCRIPTION OF THE DRAWINGS

For a better understanding of this invention, both as to its organization and as to its method of operation, together with additional objects and advantages thereof, reference is made to the following description taken in connection with the accompanying drawings, in which:

FIGS. 20A, 20B, 20C, 20D and 20E show the relationship between the scanning of the work, the displays corresponding to reflections from different depths of the work, and the display of elements selected from each display at different depths of the display.

DETAILED DESCRIPTION OF INVENTION

Figure 1:
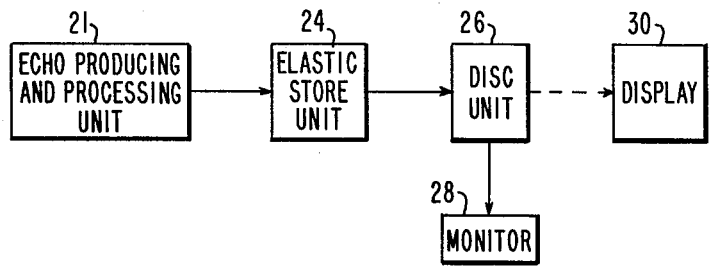
FIG. 1 is a block diagram showing the apparatus with which this invention is practiced.

The apparatus shown in FIG. 1 with which this invention is practiced includes an echo-producing and processing unit 21, an elastic-store unit 24, a disc unit 26 and a monitor 28. The echo-producing and processing unit 21 supplies intelligence of the echo patterns which it produces to the elastic-store unit 24. The disc unit 26 records on a video disc intelligence as to the echo pattern which it derives from the elastic-store unit 24. The record on the disc is recorded so that it can be displayed on a CRT display 30. As the intelligence from the elastic-store unit is being recorded, it is monitored on the monitor 28.

Typically, in the interest of convenience, the display 30 conforms to conventional television standards and the disc unit 26 produces video records consistent with these standards. The display has a picture update rate of 30 frames per second.

Each frame consists of 525 lines (2:1 interlaced) of which 480 lines are actually available for display. This means that each TV line occupies 63.5 $\mu$S, (micro seconds) of which about 53.5 $\mu$S are available for display of information. The duration of the useful portions of the acoustic returns may be as great as 160 $\mu$S when imaging deep sections of the work but may be as small as 60 $\mu$S for shallow sections.

Each acoustic return from a single position of the transducer can consist of up to 150 distinguishable picture elements, each having a maximum dynamic range of 256 levels (i.e., 8 bits of the intelligence as recorded digitally in the elastic store). In accordance with the Nyquist Sampling Theorem, a sampling rate of 150 samples per return would be adequate to retain all the information in the signal. However, a higher sampling rate is desirable to cope with instrumental imperfections and to prevent distracting beat patterns. A conventional 4 MHz TV picture is composed of about 500 samples in each TV line. Practical considerations then dictate the squeezing (or expansion) of each acoustic return into a single TV line in which the brightness of each picture element is a measure of the intensity of the transducer echo signal at the corresponding point. The position of a picture element from left to right on the monitor screen is related to the time display of each part of a return, and the position vertically on the screen corresponds from top to bottom, to successive returns from different positions of the transducer.

To accomplish this display, the time base of the acoustic echo is set to conform with the TV standard and each return is then recorded on the disc as a TV line. As the transducer subassembly 25 (FIG. 2) scans these lines they are accumulated, one return at a time, on the disc and displayed on the monitor 28. Later the disc is used to produce a display, as a picture, which is built up from top to bottom, one line at a time. Since the disc is rotating in synchronism with the TV frame rate, 30 Hz, the display of each line is refreshed 30 times per second. In order to avoid flicker, each echo is recorded on the disc in both the odd field and corresponding even field positions to provide a 60 Hz display refresh rate.

There are only 150 distinct range elements available from each return and these are displayed across the entire face of the display cathode-ray tube; a complete image consists of only 120 transducer positions (unique TV lines) on 120 elemental areas. The signal from each area is sampled 150 times. To retain correct geometrical relationships between features in the field of view, it is intended to record each sonic return as four identical TV lines, two in each field. This fills the entire display tube screen (120×4=480) and provides equivalent resolution in the horizontal (wall depth) and vertical (acoustic energy scan) directions.

Figure 2:
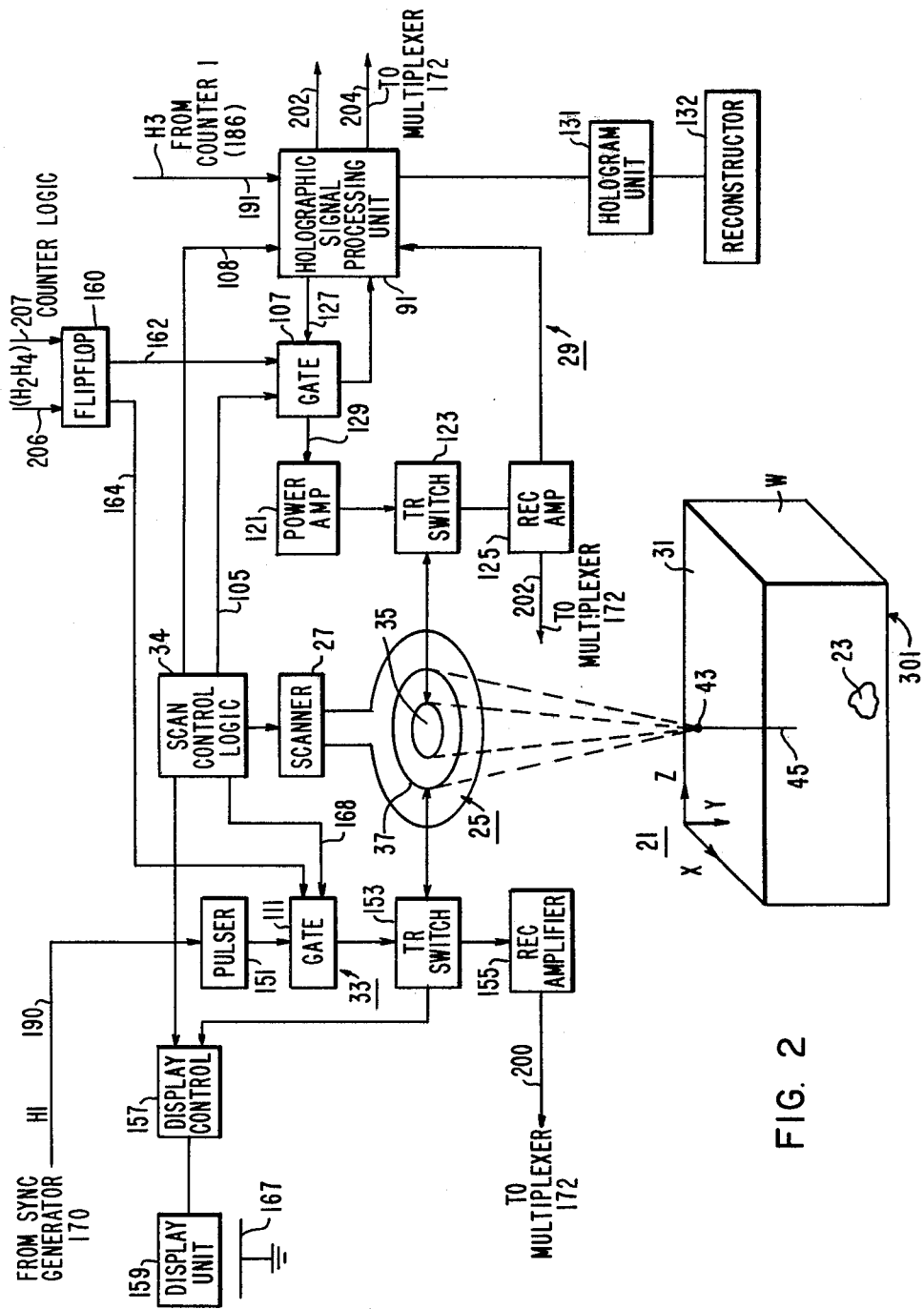
FIG. 2 is a block diagram showing echo-producing and processing apparatus which produces and processes the echoes for the display system used in the practice of this invention.

FIG. 2 shows the echo-producing and processing unit 21. This unit 21 operates to detect flaws 23 in the work W. The work W is in the form of a rectangular parallelpiped. For the sake of convenience in describing this invention, the surfaces of the work are referred to as a three-dimensional corrdinate system whose X and Z axes are along the sides of the upper surface 31 and whose Y axis is along the edges perpendicular to this surface, i.e., along the depth of the work W. A C-scan acoustic image is the image produced by scanning the X-Z coordinate plane surface or any surface parallel to it. A B-scan acoustic image is the image produced by scanning in depth parallel to the X-Y of Y-Z coordinate plane. In the practice of this invention a C-scan can be derived from a family of B-scans.

The flaw detection apparatus 21 includes a transducer subassembly 25. This subassembly is driven by scanner 27 to scan the work W. The apparatus also includes a holographic echo-processing subassembly 29 for the holographic mode of acoustic imaging and an echo-ranging subassembly 33 for the line-focused mode of imaging in which the acoustic energy is focused along a line 45 perpendicular to surface 31 of the work W. The scanner is driven and its scanning is coordinated with the operation of the holographic echo-processing subassembly 29 and of the echo-ranging subassembly by scan control logic 34. The work W is immersed in water (not shown) and the transducer subassembly 25 extends into the water propagating the acoustic energy to the work through the water. Typically the transducer subassembly 25 is about 10 inches above the surface 31.

The transducer subassembly 25 includes a point-focusing subassembly, which may be a conventional acoustic-lens transducer 35, and a focused-arc transducer 37. The focused-arc transducer is described in Hurwitz application. The acoustic-lens transducer 35 produces a beam of acoustic energy which is focused at a point 43 on or near the surface 31 of the work. A broad beam pattern diverges from the focal point penetrating into the work. Flaws in the work echoes which are propagated to the transducer 35 (or to a separate receiver-transducer) and processed. Typically, the frequency of the acoustic energy propagated by transducer 35 is 1 to 5 megahertz.

The acoustic energy from the focused-arc transducer 37 is focused along a line 45 extending along the depth of the work W perpendicular to the surface 31. At each point (elemental area) of surface 31 to which the acoustic energy from the focused-arc transducer is propagated, the acoustic energy is focused progressively along the corresponding line 45. The rate at which the surface is scanned is typically low compared to the rate at which the acoustic energy moves along line 45 so that where the movement of the scanner is continuous, the movement of the focus may be regarded as taking place along a line perpendicular to surface 31 rather than along a line at an appreciable angle to surface 31. A flaw 23 encountered by acoustic energy propagated along line 45 produces an echo which is reflected back to the transducer 37 and is processed.

Figure 10:
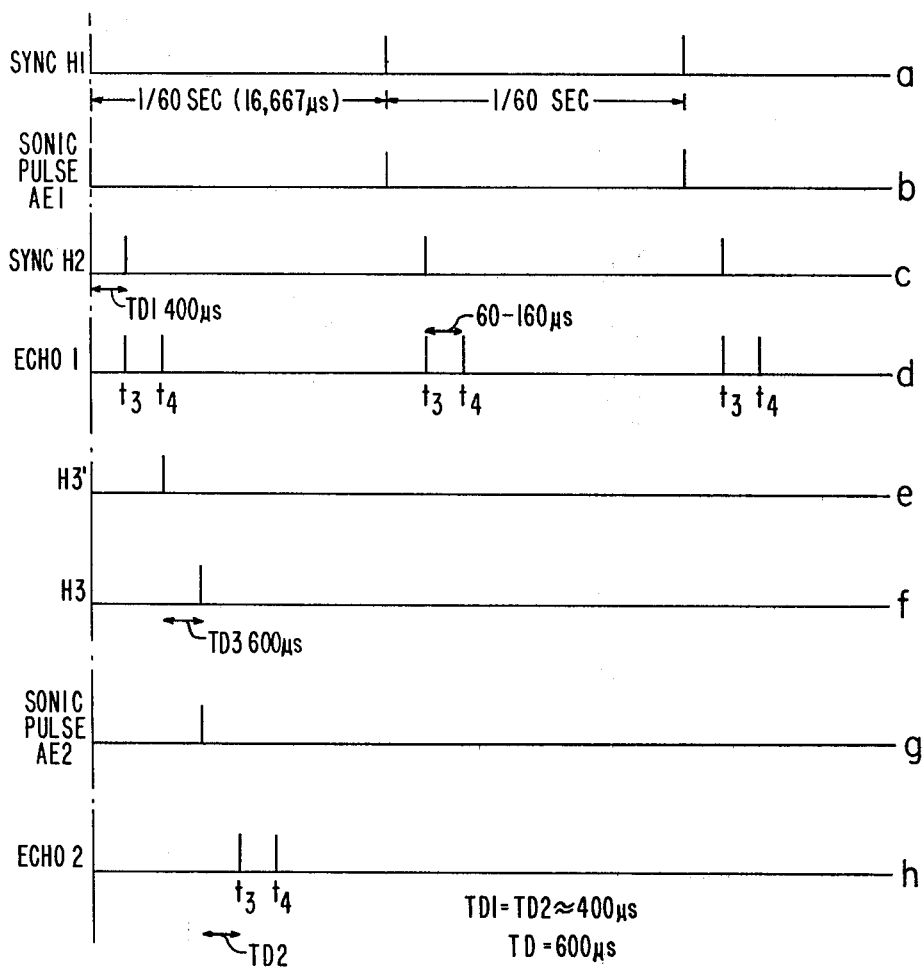
FIG. 10 illustrates coordinated graphs a, b, c, d, e, f, g, and h showing the relationship of the synchronizing pulses derived from the apparatus shown in FIG. 5, the propagated acoustic energy pulses of the apparatus shown in FIG. 2, and the echoes derived from the apparatus shown in FIG. 2.
Figure 10A:
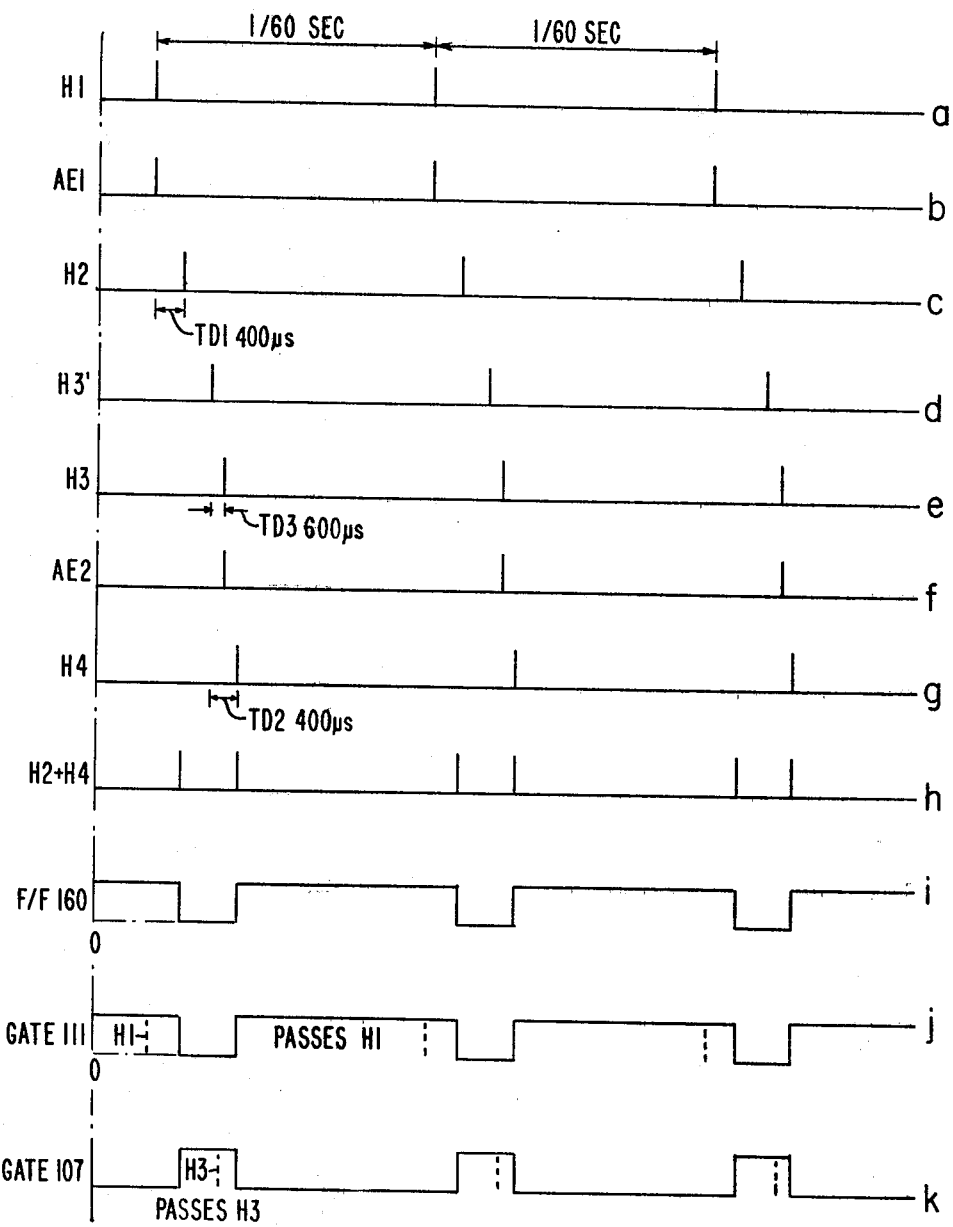
FIG. 10A illustrates coordinated graphs a, b, c, d, e, f, h, i, j and k showing the relationship between the timing pulses and the acoustic energy pulses generated in the practice of the invention and components of the apparatus of FIG. 2.
Figure 13:
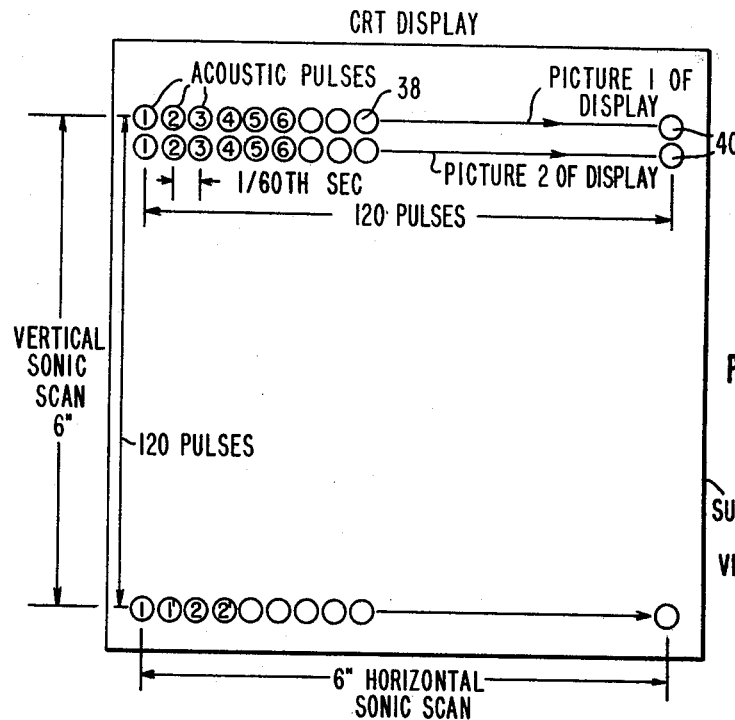
FIGS. 13 and 14 are diagrams which, taken together, show the relationship between the scanning of the work and the display of the intelligence derived from the scanning.

The scanner 27 is controlled by the scan-control logic 34 as disclosed in Hurwitz application to cause the transducer subassembly 25 to scan the surface 31 of the work W. As the transducer subassembly 25 scans the work W, acoustic energy from the acoustic-lens transducer 35 and the focused-arc transducer 37, depending on which is energized, propagates acoustic energy on elemental areas 38 (FIG. 13) of the surface 31 of the work W. Typically, the acoustic energy from the acoustic-lens transducer 35 is at each elemental area 38 focused on or near the surface 31, and the acoustic energy from the focused-arc transducer is focused along a line or pencil 43 penetrating into the work below each elemental area. As shown in FIG. 13, strips or lines 40 of the work W are successively scanned. In a typical situation where the area of the work W scanned is 6 inches by 6 inches, 120 elemental areas 38 are scanned along each strip 40, and the area is scanned in 120 strips 40 of elemental areas. In the practice of this invention, acoustic energy is during the scanning propagated on each elemental area 38 both from the focused-arc transducer 37 and from the acoustic lens transducer 35 (FIGS. 10, 10A).

The holographic echo-processing subassembly 29 includes the gate 107, the holographic signal-processing unit 91, a power amplifier 121, a transmit-receiver switch 123 and a receiver amplifier 125. Where separate transducers are provided for transmitting and receiving the T-R switch 123 may be dispensed with. The holographic signal-processing unit 91 includes the oscillator (not shown separately) which supplies the waves for exciting the acoustic-lens transducer and facilities (also not shown separately) for mixing the received acoustic signal with an electrical analog of a reference acoustical wave. The unit 91 also includes the pulser for pulse modulating the waves from the oscillator to be transmitted by transducer 35, and the sample hold for echoes received (not shown separately). The oscillator which modulates the transmitted pulses also supplies the electrical analog of the acoustical reference wave which is mixed with the received signal to produce the hologram.

When the gate 107 is open, the holographic echo-processing subassembly is enabled and the holographic signal processing unit 91, through conductors 127 and 129 and the gate 107, actuates the power amplifier 121 to transmit pulses through the T-R switch 123 to energize the acoutic-lens transducer 35. The transducer 35 transmits acoustic energy which is focused at points 43 along the scanning contour of the transducer 35. This energy spreads through the work W producing echoes at the flaw 23 which are received by transducer 35, transmitted through the T-R switch 123 and the receiver amplifier 125 to the holographic signal-processing unit 91. In the processing unit 91 the received signal is mixed with the electrical analog of the acoustical reference wave, phased in accordance with the instantaneous position of the transducer 35 during the scanning. The resultant signal is transmitted to the hologram unit 131 to produce an interference pattern on a film (not shown). This hologram is reconstructed by a laser beam in the reconstructor 132 and converted into a visual optical image. The hologram is reconstructed for monitoring purposes.

The echo-ranging subassembly 33 (FIG. 2) includes the gate 111, a pulser 151 for producing pulses to energize the focused-arc transducer 37, another transmit-receive switch 153, which may also be dispensed with if separate sensors are used, for transmitting and receiving, and a receiver-amplifier 155. In addition, there is a display control 157, a display 159, typically a cathode-ray tube, which serve for monitoring. When the gate 111 is open, the pulses are impressed on the focused-arc transducer 37 through the T-R switch 153 producing acoustic energy focused and propagated along lines 45 as the transducer 37 scans the work 31. The echoes are transmitted through the T-R switch 153 to the receiver-amplifier 155 whence they are transmitted to the control 157. The monitoring display control 157 also receives synchronizing signals from the scan-control logic 34. The echo signals are impressed, typically on the grid of the cathode of the cathode-ray tube, to modulate the cathode ray beam. Since a monitor 28 is provided for cooperation with the disc unit 26, the display 159 and the control 157 may be dispensed with if desired.

The gates 107 and 111 (FIG. 2) are opened by a flip-flop 160 alternately through conductors 162 and 164, respectively. The flip-flop 160 is actuated by pulses along lines 206 and 207 from the counter logic 166 (FIG. 5) of the elastic-store unit 24. These pulses are timed so that the holographic echo-processing subassembly 29 and the echo-ranging subassembly 33 are enabled alternately (FIGS. 10, 10A) to propagate acoustic energy to, and receive echoes from each elemental area 38 (FIG. 13) of the work W. The opening and closing of the gates 107 and 111 are coordinated with the movement of the scanner by signals transmitted from the scan-control logic 34 through conductors 105 and 168. The scanner 27 is actuated by the scan-control logic 34 to scan in both directions but the gates 107 and 111 are open only when the scanner is scanning in a selected direction to avoid backlash problems. The conductors 105 and 168 provide signals which permit the pulses to open gates 107 and 111 only while the mechanism carrying the assembly 25 (in Hurwitz application, the block 75) and the assembly are moving in the forward direction.

As shown in FIG. 2, pulses H1 (FIGS. 10, 10A) are impressed on the pulser 151 of the echo-ranging subassembly 33 through conductor 190 from sync generator 170 (FIG. 5) in the elastic-store unit 24. Pulses H3 (FIGS. 10, 10A) are also impressed on the holographic signal-processing unit 91 through conductor 191 from adjustable delay (TD3) 209 in the elastic-store unit 24. The pulses H1 on conductor 190 are effective only when gate 111 is open and pulses H3 on conductor 191 are effective only when gate 107 is open. The opening and closing of the gates 111 and 107 is controlled by the flip-flop 160 (FIG. 10A, graphs h, i, j). The flip-flop is controlled by pulses H2 and H4 (FIG. 10A, graphs c and f) from the counter logic 166 in the elastic-store unit 24 through conductors 206 and 207. As shown in FIG. 2, the holographic signal-processing unit 91 transmits its output signals to a multiplexer 172 (FIG. 5), of the elastic-store unit 24 through conductors 202 and 204 and the receiver amplifier 155 transmits its signals to the multiplexer 172 through conductor 200.

Figure 3:
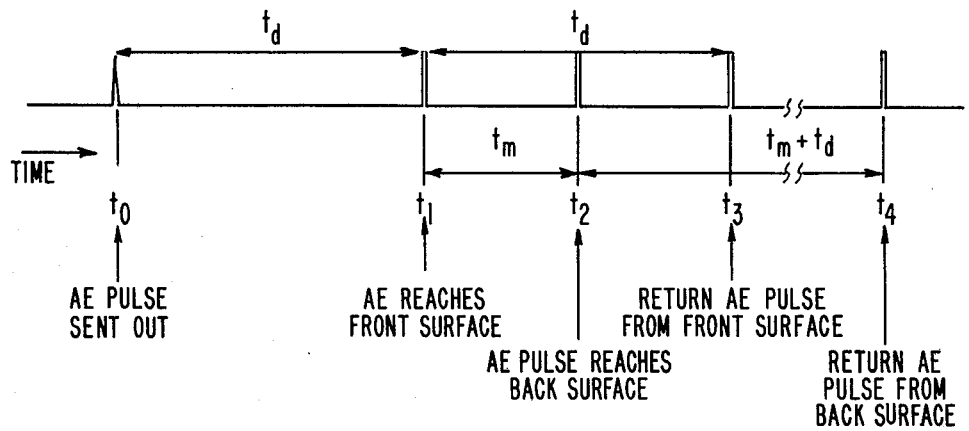
FIG. 3 is a graph showing the time relationship of the events which occur when an acoustic pulse is propagated to work.
Figure 4:
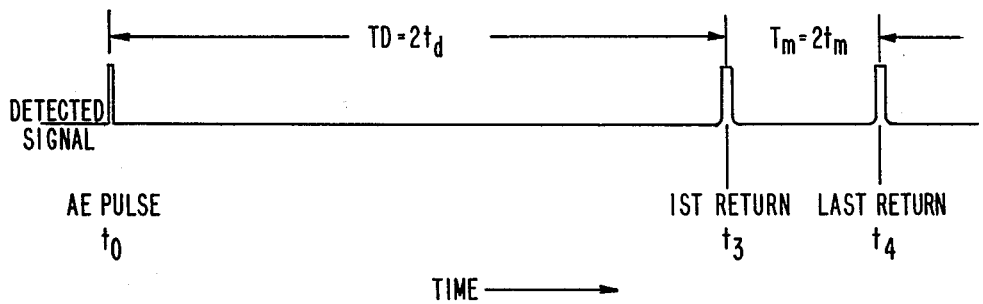
FIG. 4 is a graph showing the time relationship between the propagation of an acoustic pulse to work and the echoes from this pulse reflected by the front and back surfaces of the work.

FIGS. 3 and 4 show the time relationship of the flow of pulses to the work and the return of echoes. In each of these graphs time is plotted horizontally and magnitude of the pulses vertically. For brevity, "acoustic energy" is designated AE. FIGS. 3 and 4 present the flow of acoustic energy for only one acoustic pulse; either the acoustic energy from the focused-arc transducer 37 or the acoustic energy from acoustic-lens transducer 35.

At time $t_o$ an acoutic energy pulse is initiated which travels toward the work W, reaches the front surface of the work at time $t_1$, and continues on through the work. At time $t_2$ the pulse reaches the back surface of the work W. Due to the discontinuity at the front surface, an acoustic energy reflection occurs which arrives back at the transducer 35 or 37 at time $t_3$; similarly, the reflected pulse from the back surface arrives back at the transducer at time $t_4$. A dead time $2t_d$, occurs. This dead time is a function of the distance between the transducers and the front surface of the work. The time $t_m$ is the time taken for the pulse to traverse the work in one direction.

FIG. 4 shows the signals as received by the work transducers 35 or 37 due to reflections from the front and back surface. Any flaws in the work W shows up as signals occurring between times $t_3$ and $t_4$. For display purposes it is thus necessary to display only the signals occurring between time $t_3$ and $t_4$. However, the dead time $t_D$ ($=2t_d$) may be different for different cases so allowance must be made for adjustment of this dead time in the signal processing system. Similarly, $t_m$ may change and adjustment for this is necessary. Typically, for the usual 10-inch distance between the transducer subassembly 25 (FIG. 2) and the surface 31 of the work W, $T_D$ is about 400 μs and $t_m$ between 60 and 160 μs.

The elastic store unit 24 (FIG. 5) includes, in addition to the counter logic 166, the sync generator 170, the muliplexer 172, the adjustable delay (TD3) 209, the elastic store 180, the variable clock generator (TD5) 182, the adjustable delay (TD1) 184, the adjustable delay 185, the counter -1- 186, the counter -2- 187 and the analog-to-digital converter (A/D) 188.

FIG. 10, graphs a through h, and FIG. 10A, graphs a through k, will aid in the understanding of the operation of the elastic-store unit 24. In each of the graphs a through h at FIG. 10 time is plotted horizontally and magnitude vertically. The ponts of intersection of any vertical line through the graphs by the time axes corresponds to the same instant of time. Likewise in each of the graphs a through k of FIG. 10A time is plotted horizontally and magnitude vertically and the points of intersection by the time axes of any vertical line through the graphs corresponds to the same instant of time.

The sync generator 170 (FIG. 5) produces the sync pulses H1 which are presented in graphs a of FIGS. 10 and 10A. These pulses H1 occur at intervals of 1/60 second as indicated. Each pulse H1 generates a cycle of propagation of acoustic energy pulses both from the focused-arc transducer 37 and the focused-lens transducer 25 and the processing of the echo trains and the echos of these pulses by the subassemblies 33 and 29 respectively. It is assumed that initially the gate 111 is set by the flip-flop 160 to pass the pulses H1 and the gate 107 is closed. This is represented at left-hand end of in graphs i, j, and k of FIG. 10A. As shown in graph i, the flip-flop 160 is initially set in a setting in which conductor 164 puts out a 1 and conductor 162 a 0 (FIG. 2). In this case, as shown in graph j, gate 111 receives a 1 passing pulse H1 from conductor 190 and, as shown in graph k, gate 107 receives a zero blocking pulse H3 through conductor 191. The pulse H1 opens gate 111 (FIG. 2) and an acoustic-energy pulse AE1 is transmitted from the focused-arc transducers 37 to an elemental area 38 of the work W and the resulting echo train from the elemental area is processed by the echo-ranging subassembly 33. The acoustic-energy pulse AE1 is presented at 1/60-of-a-second intervals in graphs a of FIGS. 10 and 10A.

The pulse H1 also enables the delay 184. After time delay TD1, delay 184 produces poulse H2. The pulse H2 is initiated at the start of the interval during which reflections from the work W are being received, i.e., just after the interval TD1. The pulses H2 are shown in graphs c of FIGS. 10 and 10A. As indicated in FIG. 10 the interval TD1 is about 400 $\mu$s. This is the dead time, assuming flow of acoustic energy in water, for a spacing between transducer assembly 25 and work W of 10 inches.

Figure 6:
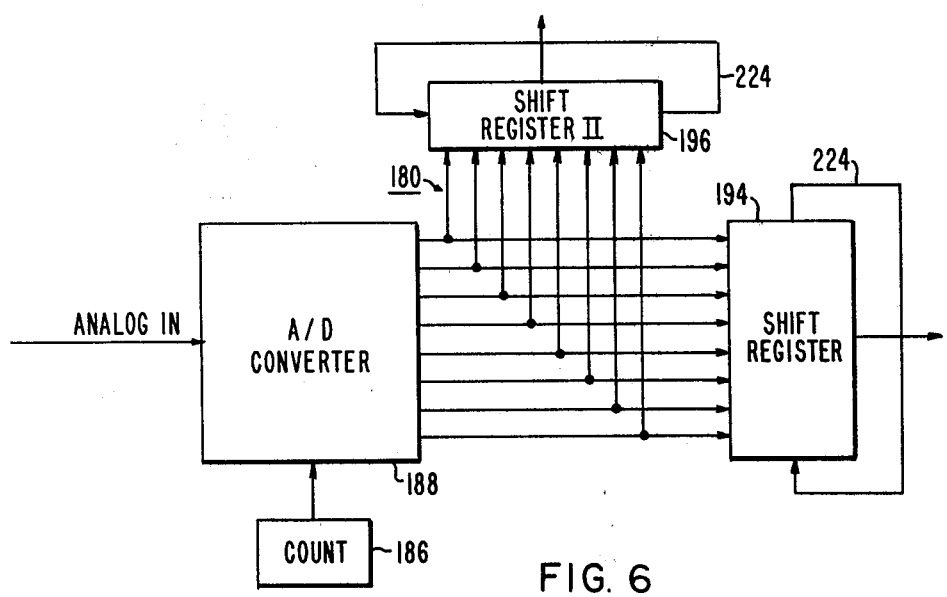
FIG. 6 is a block diagram showing the analog-to-digital converter of the apparatus shown in FIG. 5 and the manner in which it cooperates with the elastic store.

When delay 184 times out at the end of interval TD1, it enables counter -1- 186. Counter 1 passes counts from variable clock generator 182 to the counter logic 166. The intervals between counts may be set to a desired magnitude. Counter 1 enables counter logic 166 which performs several functions. For each count from clock generator 182 counter 1 enables the multiplexer 172 by signals along conductor 163, to pass a sample of the echo train received on conductor 200 from the elemental area 38 to which the acoustic-energy pulses AE1 was propagated. The counter logic 166, by signals along conductor 165, also enables the A/D 188 (FIG. 6) to receive the samples from the echo train from the multiplexer and to convert these samples into a set of numbers. Typically, where there are 150 samples per echo train, about 149 or 148 or 147, or even fewer, samples are at this point converted. The number of samples converted depends on the number reserved for the echoes from the holographic echo-processing subassembly 29. The counter logic by a signal along conductor 167 enables the elastic-store 180 to store the output of the A/D 188. The echo train which has been reflected during the interval $t_3$–$t_4$ is processed in this way (graph d FIG. 10). The counter logic 166 also transmits the pulse H2 along conductor 206 to the flip-flop 160 (FIG. 2) causing its output 164 to flop to 0 (graph j FIG. 10A) and the output 162 to flop to 1 (graph k FIG. 10A). This occurs after the complete echo train from the elemental area 38 impinged by the acoustic-energy pulse AE has been processed by the echo-ranging subassembly 33.

At the end of the number of counts 149, 148, or 147 as the case may be, selected for sampling the echo train from the elemental area to which the acoustic energy was propagated by the focused-arc transducer 37, counter 1 transmits a pulse H3' to delay 209 starting the delay to time out. This pulse H3' is represented in graph d of FIG. 10A and graph e of FIG. 10. Delay TD3 times out in about 600 $\mu$s, as indicated in FIG. 10, producing pulse H3. Pulse H3 is represented in graph e of FIG. 10A and in graph f of FIG. 10. Pulse H3 is impressed on conductor 191. At the time flip-flop 160 (FIG. 2) has flopped to zero (FIG. 10A graph i) so that the output at conductor 162 is 1 (FIG. 10A graph k) and the output at conductor 164 is 0 (FIG. 10A graph j). Gate 107 is then opened and pulse H3 (see broken line FIG. 10A graph k) produces acoustic-energy pulse AE2 (FIG. 10A graph f).

The 600 $\mu$s delay between the end of the count of counter 1 and the initiation of the acoustic energy pulse AE2 is required to afford time for the acoustic energy produced by pulse AE1 to decay completely. The energy reflected by the surface 301 (FIG. 2) of the work W remote from the surface 31 and by any flaw 23 is not entirely propagated through the surface 31. An appreciable portion (about 10% typically) of this energy is totally reflected at the surface 31 and again reflected from the surface 31 to the surface 301. A fraction of this latter energy is then again reflected by surface 301 and a part transmitted through surface 31 and a part reflected. This process is repeated until the energy in the work decays to a very low magnitude. The 600 $\mu$s plus the 200 $\mu$s ($lt_d$, FIG. 4) during which the energy flows from the transducer subassembly to the work affords time for the energy from the focused-arc transducer 37 to decay to this very low magnitude.

Pulse H3 is also supplied to delay 185 to enable this delay to time out. After the time interval TD2 which is typically about 400 $\mu$s, counter -2- 187 is enabled by pulse H4 to transmit counts from clock generator 182 into counter logic 166 through conductor 193. The pulses H4 are presented in graph g of FIG. 10A. Counter logic 166 then enables multiplexer 172 to pass the selected number of samples of the outputs of conductors 202 or 204 from the holograph signal-processing unit 91 (FIG. 2) to the A/D 188. A sample is passed for each count of counter 2. The counter logic 166 also enables the A/D through conductor 165 to pass the last-mentioned samples in digital values to the elastic store 180. The counter logic 166 also transmits the pulse H4 to the flip-flop 160 (FIG. 2) to reset the flip-flop as shown at the end of the first pulse on the left in graphs i, j, k of FIG. 10A. Pulses H2 and H4 are shown together in graph h of FIG. 10A. As can be seen the duration between them is the duration of the negative pulse of flip-flop 160. Flip-flop 160 is only reset after the acoustic energy from the acoustic-lens transducer 35 has been completely processed by the holograhic echo-processing subassembly 29. One cycle of the processing and storing of echoes is now completed. The next cycle is started by the second pulse H1.

Figure 5:
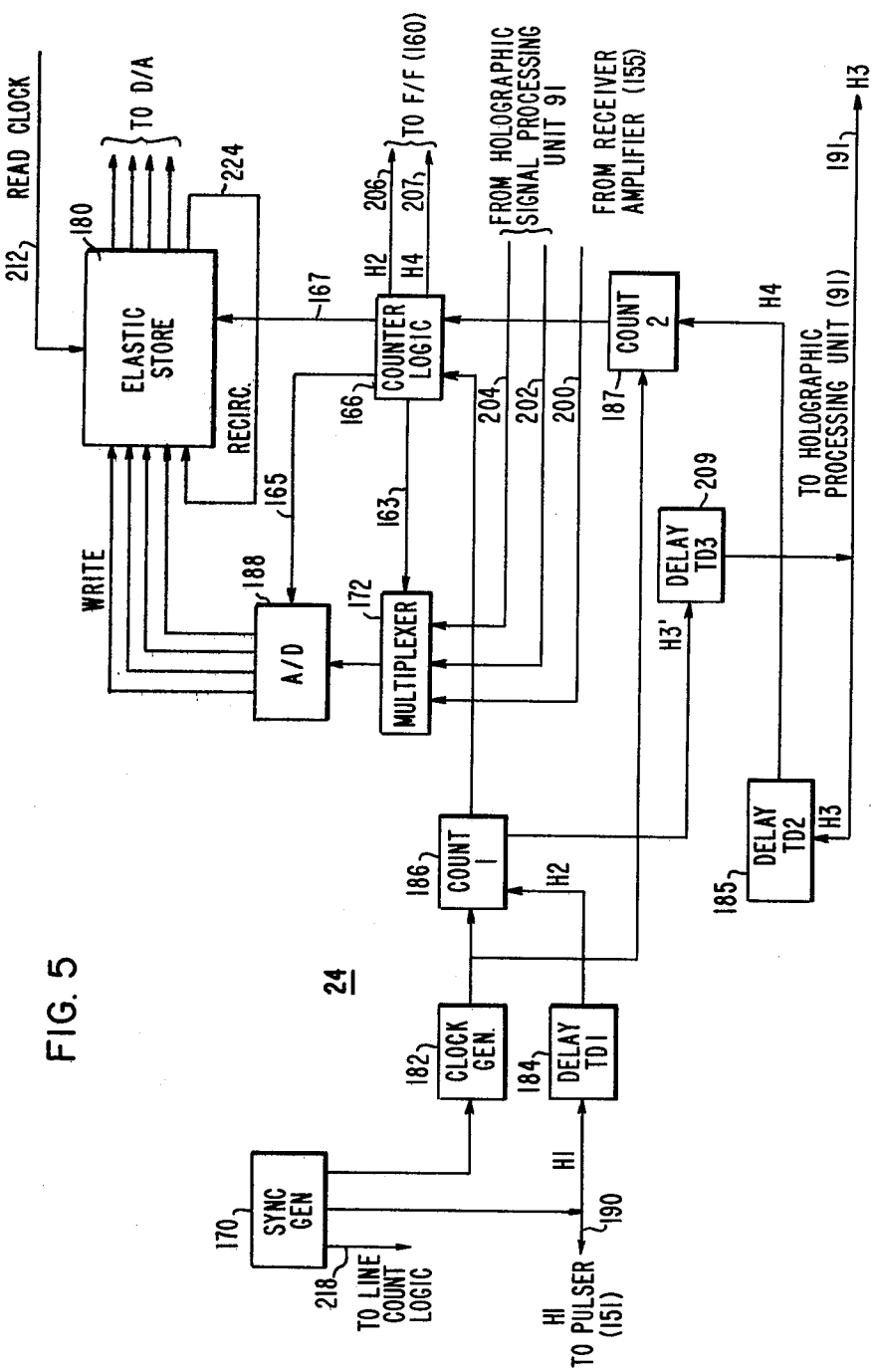
FIG. 5 is a block diagram of the elastic store unit showing the cooperative relationship between the elastic store and the apparatus shown in FIG. 2 and the manner in which the intelligence from the apparatus shown in FIG. 2 is stored in the elastic store.

FIG. 5 shows one conductor 200 from the receiver amplifier 155 of the echo-ranging subassembly and a plurality of conductors 202 and 204 from holographic signal-processing unit 91. In the interest of brevity only one output for the processing unit 91, i.e., only one holographic channel, is shown in FIG. 2. It is contemplated, however, that there may be more than one holographic channel availing signals for processing. The multiple holographic intelligence may be provided by a plurality of focused-lens transducers focused at different depths of the work or by a plurality of different range gates set to pass intelligence for different depths of the work W. The counter logic 166 switches the multiplexer 172 from one of the conductors 200, 202, or 204, to the other when activated by pulses from the counters 186 and 187. This switching is coordinated with the operations of the flip-flop 160 (FIG. 2) to which the counter logic 166 is connected through conductors 206 and 207. The counter logic 166, when actuated, also enables the A/D 188 to accept the selected magnitudes.

Figure 7:
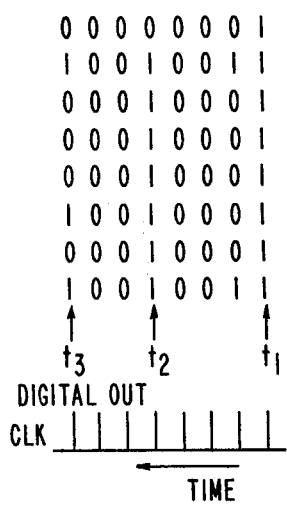
FIGS. 7 and 8 are graphical diagrams illustrating how the magnitudes corresponding to the echoes from the apparatus shown in FIG. 2 are stored in the elastic store.
Figure 8:
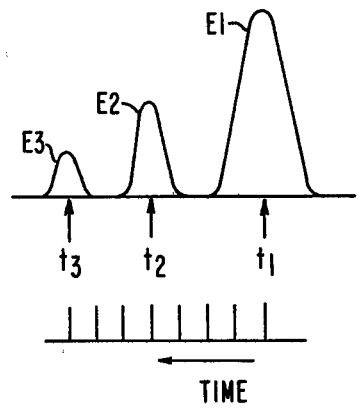

FIGS. 7 and 8 illustrate the operation of the A/D 188. Let it be assumed that acoustic energy focused along a line or pencil 45 penetrating into the work W has produced an echo train including the strong echo E1 at time $t_1$ of the clock 182, the medium echo E2 at time $t_2$, and the weak echo at time $t_3$. $t_1$ is the earliest instant and $t_3$ the latest. The resulting magnitudes which are supplied by A/D 188 to the elastic store 180 are as shown in FIG. 8: E1=255, E2=127, and E3=69. The significance of the bits in the table in FIG. 7 increases from the bottom to the top.

Figure 9:
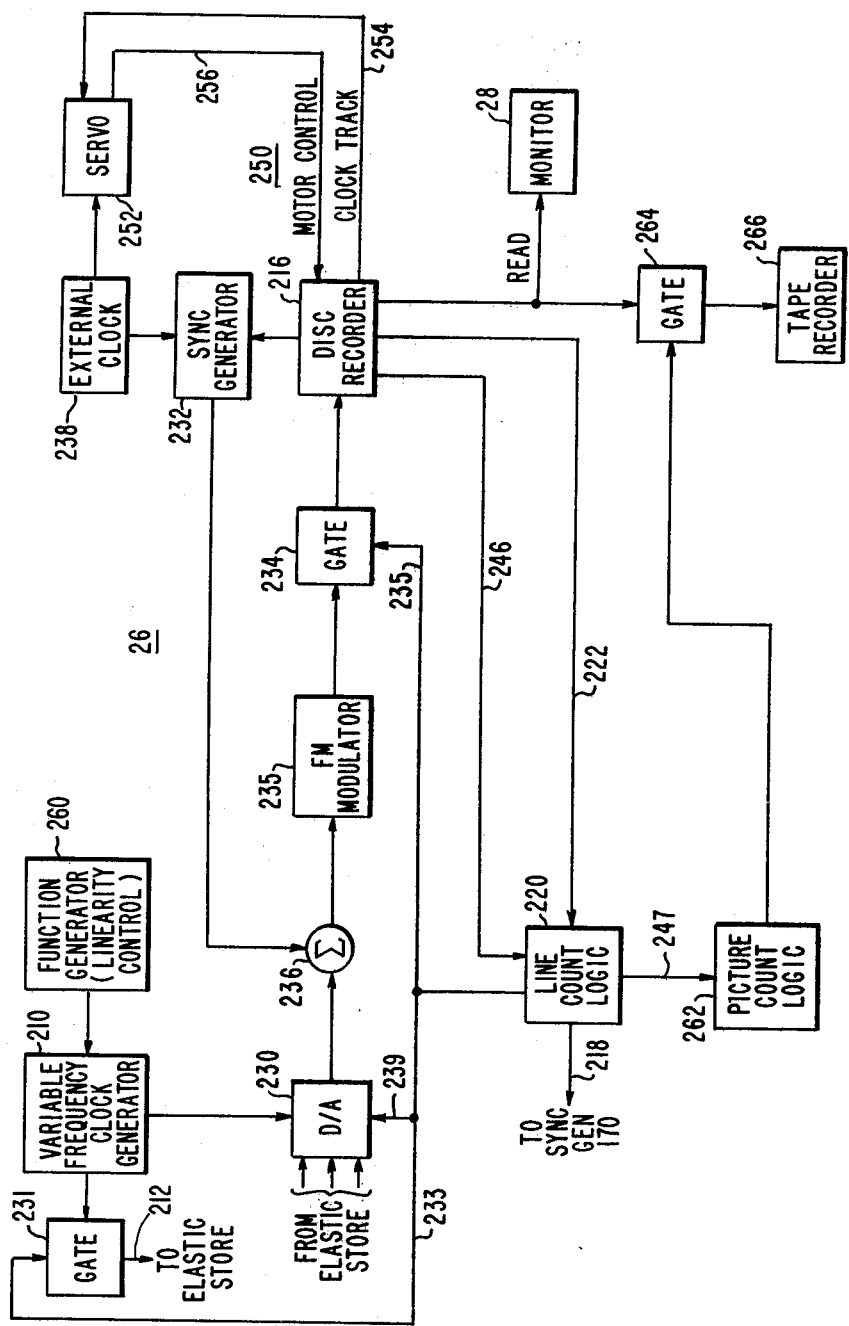
FIG. 9 is a block diagram of the disc unit showing how the intelligence stored in the elastic store is recorded on a video disc or other video record.

Typically, the flip-flop 160 (FIG. 2) enables the echo-ranging subassembly 33 and the holographic echo-processing subassembly 29 to propagate acoustic energy to, and to process echoes from, each of a succession of elemental areas 38 (FIG. 13) of the work W. The elastic store 180 (FIG. 5) stores the echo data from the elemental areas 38 irradiated with acoustic energy during one complete cycle of the flip-flop 160. The binary numbers shown in FIG. 7 correspond to this one cycle. The recording includes the magnitudes of the components of an echo train derived from receiver 155 and the magnitude of the echo from the holographic signal processing unit 91.

each set of data from each of the succession of elemental areas is transferred from the elastic store 180 to the video disc in the disc unit 26 (FIGS. 1, 9). The elastic store is enabled to effect the transfer by a READ signal from a variable-frequency clock generator 210 in the disc unit 26 (FIGS. 1, 9) through conductor 212. The pulsing of the sync generator 170 (FIG. 5) is coordinated with the operation of the disc recorder 216 (FIG. 9) by a signal along conductor 218 from the line count logic 220 of the disc unit 26. The line count logic 220 is controlled by a signal from the disc recorder 216 along conductor 222. The signal on line 218 resets the sync generator 170 to transmit its pulses (FIG. 10, graph a; FIG. 10A, graph a) after each transfer of the intelligence in the elastic store 180. The unit of intelligence in the elastic store 180 which is transferred during each transfer and recorded on disc 240 (FIG. 11) in the disc unit 26 corresponds to the intelligence unit displayed by four interlaced lines on the CRT, each line containing the same intelligence. The recording on the video disc 240 provides for transfer to the CRT of 60 full pictures per second, one set of 30 pictures being interlaced with a second set. To achieve this purpose the elastic store 180 includes two shift registers 194 and 196 (FIG. 6), which operate alternately to receive intelligence from A/D 188 and transfer this intelligence to disc 240. The line-count logic 220 counts the lines which are recorded by the disc recorder and appropriately resets the sync generator 170. Since the pair of echoes each consisting of an echo train from echo-ranging subassembly 33 plus an echo from holographic echo-processing subassembly 29 is to be recorded on the disc 240 so that it is to be displayed as four lines of the CRT, digital gates (not shown) connect the outputs of each shift register 194 and 196 to the input through conductors 224.

The signal as sampled is in excess of 150 times during the signal period between times $t_3$ and $t_4$ (FIG. 4) and an analog-to-digital conversion is made each time the signal is sampled. The clock pulse generator 182 is used to generate the digital pulses first through counter 1 for the echo train from the echo-ranging subassembly 33 and then through counter 2 from the holographic echo-processing subassembly 29. Then the generator 182 stops the A/D conversion. The clock pulse generator runs continuously, but the counter is initiated by the synchronizing pulses H2 and H4. The time $t_m$ depends upon the thickness of the object being examined, to allow for this the frequency of the clock pulse generator 182 is made adjustable.

The disc unit 26 (FIG. 9) includes in addition to the monitor 28, the variable-frequency clock generator 210, the disc recorder 216, and the line count logic 220, the digital-to-analog converter (D/A) 230. The D/A 230 converts the magnitudes from the elastic store 180 into electrical signals proportional to the echo amplitudes. There are also the gate 231, the additional sync generator 232, an adder 236, an FM modulator 235, and an additional gate 234 connected to the disc recorder 216.

The sync generator 232 is driven by an external clock 238. The disc recorder 216 includes the video disc 240 (FIG. 11) with circular tracks 242 for recording intelligence. The recorder 216 also includes a recording-replay relay heads, amplifiers and other facilities (not shown) for producing video records on the tracks.

As has been disclosed, the echo-ranging subassembly 33 and the holographic echo-processing subassembly 29 produce respectively in succession an echo train signal and an echo signal from each elemental area 38 (FIG. 13) of the work W. These signals for each successive area are stored in the elastic store 180 and read out, and stored as a CRT line on a selected track 242 of the disc 240. This intelligence for each CRT line is stored on a predetermined segment 244 (FIG. 11) of the selected track 242 of the disc 240. To carry out this stage of the method according to this invention the predetermined segment 244 of the track 242 is moved under the recording/playback relay head (not shown) and the intelligence of the elastic store 180 (one of the shift registers 194 or 196) is transferred to the D/A 230 and recorded in the segment 244. The intelligence is assembled in the elastic store 180. TV synchronizing pulses from the sync generator 232 (FIG. 9) are added to the intelligence from the D/A 230 by the adder 236 and after filtering the composite signal is passed to an FM modulator 235. This modulator generates a signal closely above the video passband, typically deviating from 4 Mhz (mega Hertz) at sync tips to 7 Mhz at white. The FM signal is saturation-recorded into the magnetic surface coating of the disc 240 (FIG. 11) in the predetermined segment 244 (typically 1/20 inch) reserved for that particular line. The feedback conductors 224 (FIGS. 5, 6) connect the outputs of each shift registers 194, 196 to the inputs so that after each reading the intelligence is restored in the shift register until four readouts of the same intelligence has been completed. Of the four readouts, two are recorded in successive segments 244 on a track 242 of the disc 240 in a first position. Then after the disc has completed approximately half a revolution, the readout process is repeated to fill in the two additional segments 244. The first two recorded segments 242 correspond to two lines during a first scanning of the field of the CRT and the second two segments correspond to the two lines of the intervening field which interlace the first two lines. This record on faces in segments 244 of the video disc is derived from one of the shift registers, say 194. The pulse repetition of the transducers 35 and 37 is controlled by the disc 240 (in the disc recorder 216) through conductor 222 and the line-count logic 220.

The transfer of intelligence, from the elastic store 180 to the disc recorder 216 is controlled by the gates 231 and 234. The intelligence is converted into analog values by the D/A 230. Both gates 231 and 234 are opened by signals from the line-count logic 220 along conductors 233 and 235. The line-count logic through conductor 239 also enables the D/A 230 to transfer the converted analog signals to the disc recorder 216.

When the gate 231 is opened by a signal from the line-count logic 220, counts from the variable-frequency clock generator 210 clock the signals at the time in the elastic store into the D/A. Since the D/A is then enabled and the gate 234 is open these signals, FM modulated, are transferred to the disc recorder 216.

The echo intelligence from the elemental area 38 following the area first processed may be processed as just described for the elemental area processed. The magnitudes from the new elemental areas are stored in the elastic store and then recorded on the disc 240 in the next two line segments in each field (four segments in all). This time the intelligence is recorded in shift register 196 and transferred from there. As the process continues, a record for a full picture, four line segments at a time, is recorded on the track 242 on the disc 240. Typically, a picture is recorded in about four seconds.

Except during actual writing of TV or CRT lines on segments 244 of the disc 240, the recording head (not shown) is in the replay setting and a display is produced on the monitor 28. The operator can monitor the picture as it unfolds. The monitor 28 includes a preamplifier, equalizer, limiter, and demodulator (all not shown). The FM signal is processed by these components (with gamma adjustment and color contouring if desired) and displayed.

To assure that the echo components of the echo trains and the holographic echo be recorded on disc 240 and displayed in the correct relative positions, a servo loop 250 (FIG. 9) for the disc is provided. This loop includes the servo 252. To derive the servo error the external clock 238 is provided with a crystal-controlled oscillator (not shown). The output of this oscillator is compared in servo 252 with a clock-track output derived through conductor 254 and the necessary correction is effected through motor-control conductor 256.

In flaw investigating, applications, involving cylindrical work W, in which the center of scan of the transducers 35 and 37 can be set at center of curvature of the work, nonlinear readout of the elastic store 180 can be avoided. In this event, proper alignment of the recorded information on the disc 240 can be assured by using the actual signal from the clock track to read the elastic store 180. When the center of scan of the transducers 35 and 37 cannot be placed at the center of curvatute of the work, linear readout of the elastic store 180 can be achieved by varying the frequency of the variable-frequency clock generator 210 in accordance with the setting of a function generator 260. The line-count logic 220, through conductor 246, also counts the recorded segments 244 on disc 240 and, through conductor 218 (FIG. 5) resets the sync generator 170 (FIG. 5) in the elastic-store unit 26. The line count logic 220 also enables picture-count logic 262 through conductor 247. When a predetermined number of pictures have been counted, the picture-count logic 262 opens a gate 264 which causes the record in the disc 240 to be recorded on a tape (not shown) in a tape recorder 266.

Figure 11:
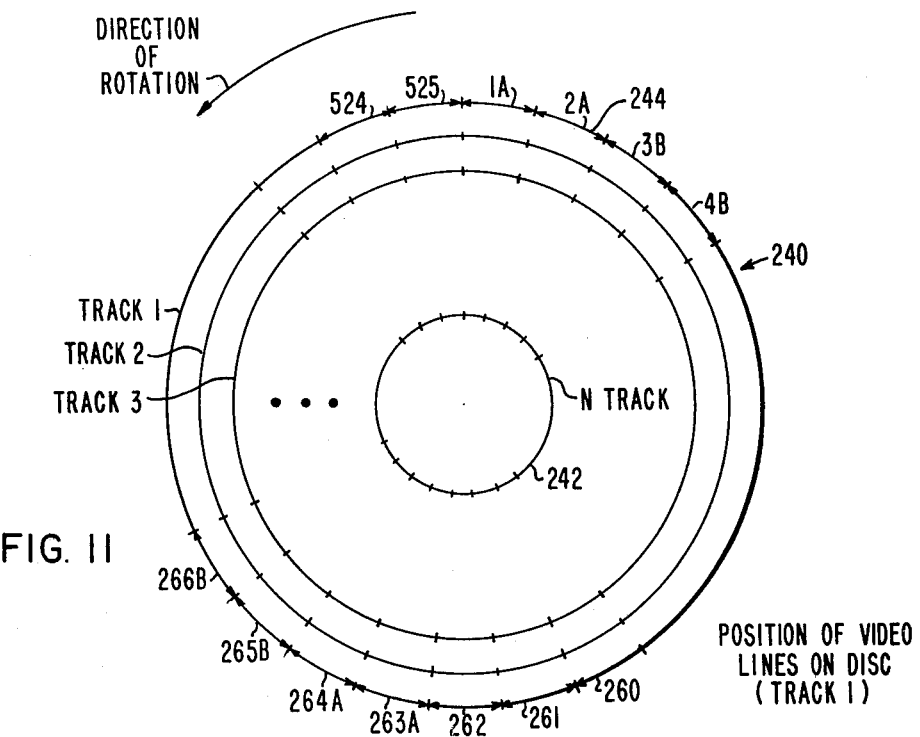
FIGS. 11 and 12 are diagrams showing the manner in which the intelligence derived from the apparatus shown in FIG. 2 and from the elastic store is recorded on a disc.
Figure 12:
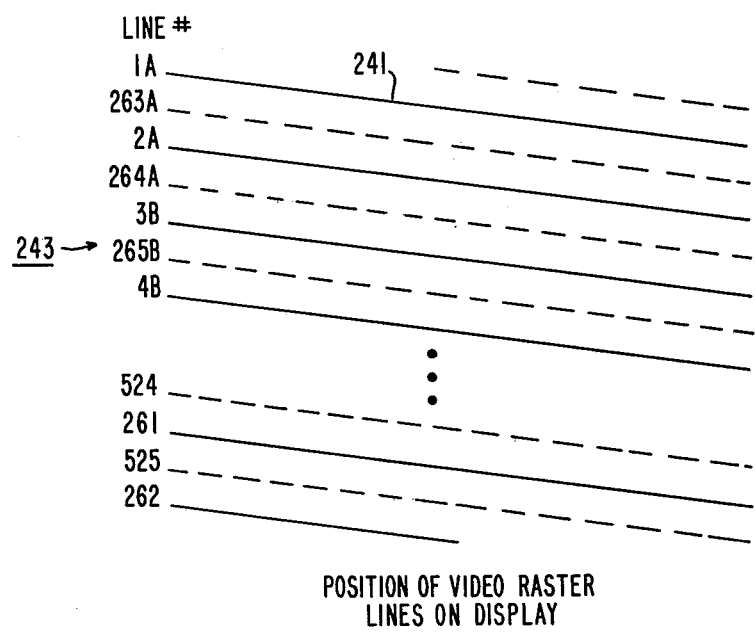

FIGS. 11 and 12 show the manner in which the record is produced on the video disc 240. The disc 240 has a plurality of circular tracks 242 numbered 1 to N. It is assumed that the record is produced on track 1 of the disc. The segments 244 on any track, say track 1, on which the complete intelligences from the elastic store 180 at any time are recorded, are numbered 1, 2, ... 525, corresponding to the 525 TV lines. To designate specific segments these numbers are followed by letters A or B. Initially the elastic store 180 contains, say in shift register 194, (FIG. 6), the echo data or intelligence from the first elemental area 38. This data includes a plurality of 8-digit binary numbers, most of the plurality being proportional to echoes processed by the echo-ranging subassembly 33 and one or several processed by the holographic echo-processing subassembly 29. This data is recorded on segments 1A and 2A of the disc 240. Then the disc is rotated about 180° and the same intelligence is recorded on segments 263A and 264A. Then the elastic store 180 receives the intelligence from the next elemental area 38 (FIG. 13) in the other shift register 196. This intelligence is recorded in segments 3 and 4 and 265B and 266B. This process is repeated until the complete intelligence for the scanning of a strip or line 40 (FIG. 13) of the work W is recorded on segments 244 of track 1. This record produces a complete TV picture consisting of two interlaced fields each repeated 30 times per second.

Figure 14:
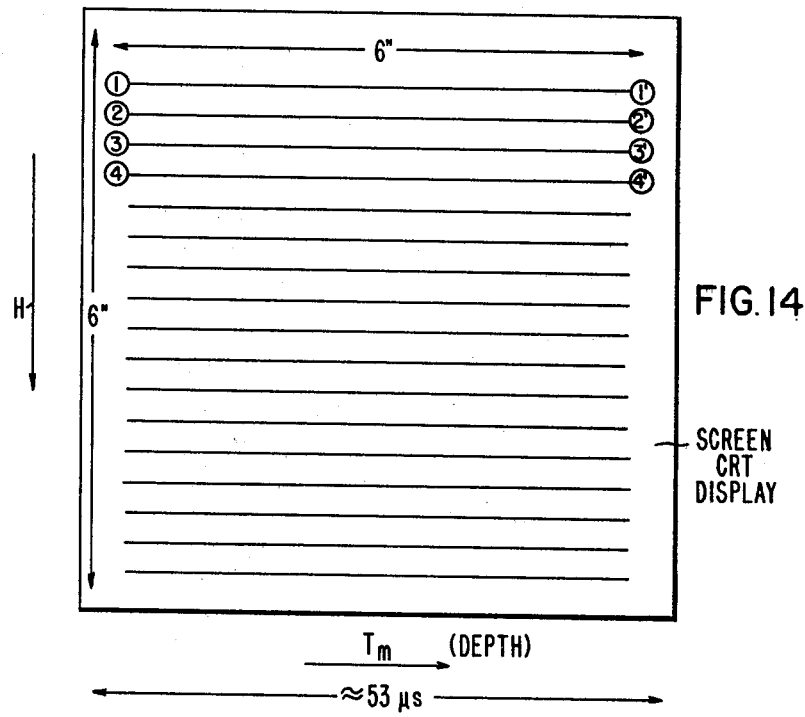

FIGS. 13 and 14 illustrate the relationship between the scanning by the transducer assembly 25 and the picture display on the CRT of monitor 28 or subsequently on a CRT or TV screen. Adjacent elemental areas scanned by this transducer assembly are identified by numbers, the first area 1, the second 2, etc. Each area is in its turn impinged by the acoustic energy from the focused-arc transducer 37 and by the acoustic energy from acoustic-lens transducer 35. The echos of the echo train reflected along pencil 45 (FIG. 2) resulting from the propagation from the focused-arc transducer 35 and the holographic echo resulting from the propagation from the acoustic-lens transducer make up the record of one line 40 on the disc 240 and one set of 4 lines on the CRT. The holographic echo is at the end of the line. Where several holographic echos are derived from different depths of the work W, there are several successive holographic echo reproductions at the end of the line 40. This is brought out by the numbering of the small circles in FIG. 14 which shows diagrammatically the CRT display. The number 1 is the first line corresponds to the number 1 in the first line of FIG. 13 and designates the reproduction in this first line of the CRT of the echo train from the first elemental area scanned. The number 1' at the end of the first line of FIG. 14 designates the reproduction of the holographic echo from the first elemental area in the first line of FIG. 13. The numbers 2 and 2' in FIG. 14 designate the reproduction of the echoes from the area 2 in the first line of FIG. 13. The other circles 3 and 3', and 4 and 4', etc., of FIG. 14 correspond to areas 3, 4, etc., of the first line of FIG. 13. A complete picture is recorded on the track 1 of record 240 and reproduced on the CRT for the first scanned line or strip 40 of the work W.

After the first picture is recorded on a track 242 the recording/playback head on the disc 240 is stepped to a new track, say track 2. The transducer subassembly 25 then returns back to the starting position and steps to an adjacent position to start a new sweep. The entire time-equivocation and line-accumulation procedure is repeated for the new sweep over a strip 40 of the work and another image is built up on the disc and monitor screen. There is expected to be a maximum of 120 sweeps (i.e., pictures) from a particular location (suspected of a flaw) on a vessel wall and each will be recorded on a separate track of the disc 240. At the conclusion of the entire recording procedure, the pictures can be inspected one at a time for as long as is desired and photographs taken of any key pictures as required. FIG. 12 shows the relationship between the records on the segments 244 of disc 240 in FIG. 11 and the lines 241 on the CRT display 243. The numbers followed by A designate recordings of and a display of the same intelligence; the numbers followed by B designate repeated recording of another item of intelligence. The four lines 1A, 263A, 2A, 264A contain the intelligence from the first elemental area 38 (FIG. 3); the lines 3B, 265B, 4B, etc., contain the intelligence from the second area 38.

The entire contents of the disc (120 pictures) can be transferred to a standard video tape and typically need occupy little more than 4 seconds of continuous recording space. The disc can than be erased and the entire procedure repeated at the location of another suspected flaw. At this rate, and with a 2-second lead-in for each segment, a 10-minute video cassette can contain a complete pictorial record of as many as 100 suspected flaw locations which can be kept on file for future reference.

The cost of a standard cassette of this size is about $15; it is probably the least costly form in which to retain the complete record. The size of the cassette is about 25 cubic inches and could contain about 12,000 pictures. This represents a storage packing density of more than 600 pictures per cubic inch at a storage cost of 8¢ per picture. Of course, 60-minute cassettes costing $25 are available in the same size, giving an ultimate packing density of 3600 pictures per cubic inch at a cost of about 3¢ per picture. When it is desired to review the contents of a cassette, the tape is played back until the particular segment of interest is located. Then the output of the video cassette player is connected to an auxiliary input of the video disc recorder and the particular pictures of interest are viewed from the disc in a conventional "stop-action" mode.

Since the output from the sonic transducer has an information capacity that is considerably smaller than the capacity of the elastic storage and disc system, the replayed signals are a good rendition of the original signals. Thus, any processing which is desirable to enhance the visibility of features in the pictures can be carried out after the disc-recording process, the effect can then be viewed immediately on the monitor 28 and without alteration of the stored information.

There are two forms of processing that are deemed valuable at this time: gamma adjustment and color contouring. The term gamma adjustment refers to nonlinear amplification in which typically the gain of intense signals (whites) is reduced and the gain of less intense signals (greys) is increased correspondingly. The term color contouring refers to the display of different brightness slices in different colors on a color monitor to render contours of features in the picture more apparent to the eye. Both functions take place at the input to the moniotor 28 so that experimental adjustments do not affect the recorded information on the disc 240 and the effectiveness of the processing can be judged directly. The signals that are eventually transcribed onto tape can be processed or not at the discretion of the operator.

There is another form of signal processing that is expected to be of value. That is the reduction of distortions that arise if the physical motion of the sonic transducer does not conform to the shape of the wall of the work W. These distortions are a function of the radius of curvature of the wall and of the center of scan of the transducer. The pictorial effect is an apparent lengthening and foreshortening of the wall thickness as a function of the displacement of the centers of curvature.

This distortion can be reduced by providing a nonuniform rate of readout of the elastic store 180. The effective position along the TV line of features at uniform form depth in the wall is adjusted by altering the frequency of the read clock 210 (FIG. 9) of the disc unit 26 by means of the function generator linearity control 260. Simple parabolic and tilt adjustments can be provided and a signal jack can be made available for supply of more complex functions when the need and desirability are established.

This adjustment of timing of the information is accomplished prior to recording so the record on the disc contains this predistortion. Provision can be made for adjusting the amount of predistortion required for a particular combination of wall and scanner location by means of trial runs on single images with the effect being viewed on the monitor.

The display system described to this point provides, on the TV monitor 28, during the recording of each track 242, a raster display of the information received from the 120 sonic pulses during a scan of the transducer along one strip (40 FIG. 13) of the work W. In addition, images resulting from scans of 120 strips are assembled on adjacent tracks on the disc surface. Consequently, at this point, all the information pertaining to the complete scanned volume of the work W is in memory, i.e., stored on the disc surface. If the head replays these tracks successively, then the complete contents of the memory is read in 4 seconds.

In accordance with a further aspect of this invention elements are selected from each of the 1 through N tracks 242 (FIG. 11), i.e., from the 1 through N CRT displays, to compose a new record for a new CRT display. These elements are recorded on another track 242 (say N+1) of the disc 240, or on a track of another disc, using another head. For example, the $i^{th}$ picture element in each track and on each CRT line, from the first set of recordings and displays, is stored in an elastic store 180 through an A/D converter, and then read out on 1st, 2nd, 263rd and 264th segments of the new track (N+1). This corresponds to the first set of interlaced lines on the CRT. Then the moving head steps to the next track and the $i^{th}$ element on this track is processed similarly and written as in segments 3, 4 and 265 and 266 for the second set of lines of the new CRT picture. When this process has been repeated for all the tracks from the sonic scan, a new record is produced from which a CRT picture can be derived showing an echo image of a plane of the work W at right angles to the scanning beam, at a depth in the wall of the work W proportional to "i." To retain geometric fidelity, each "unique" CRT line generated in this manner is recorded on the new track and displayed as four TV lines in the new picture.

Among the $i^{th}$ elements which can be selected are the holographic elements identified by the primed numbers in FIGS. 13 and 14. In the case of these elements a hologram is produced rather than a display on a CRT. The hologram can be reconstructed in the usual manner. The reconstruction may be digital reconstruction in a computer or array-processing by illumination of a transparency hologram with a laser beam or by illumination of a reticon tube or other reflective CRT display of the hologram with a laser beam.

The orthogonal transformation of the image plane provides an effective depth-of-focus in the new picture which is as narrow as the range resolution of the acoustic-energy system and is not contaminated by out-of-focus reflectors. If desired, the depth of focus of the transformed image can be increased at will simply by integration of the $i^{th}$ through $j^{th}$ picture elements from the original pictures. If the parameter "i" is varied during the described procedure, the new image plane can be at any arbitrary angle to original acoustic-energy beam or even curved as required. If a second video record/replay head is used to accumulate the transformed picture and is mounted on a moving assembly, many transformed images can be created. Each transformation process typically requires 4 seconds.

Figure 15:
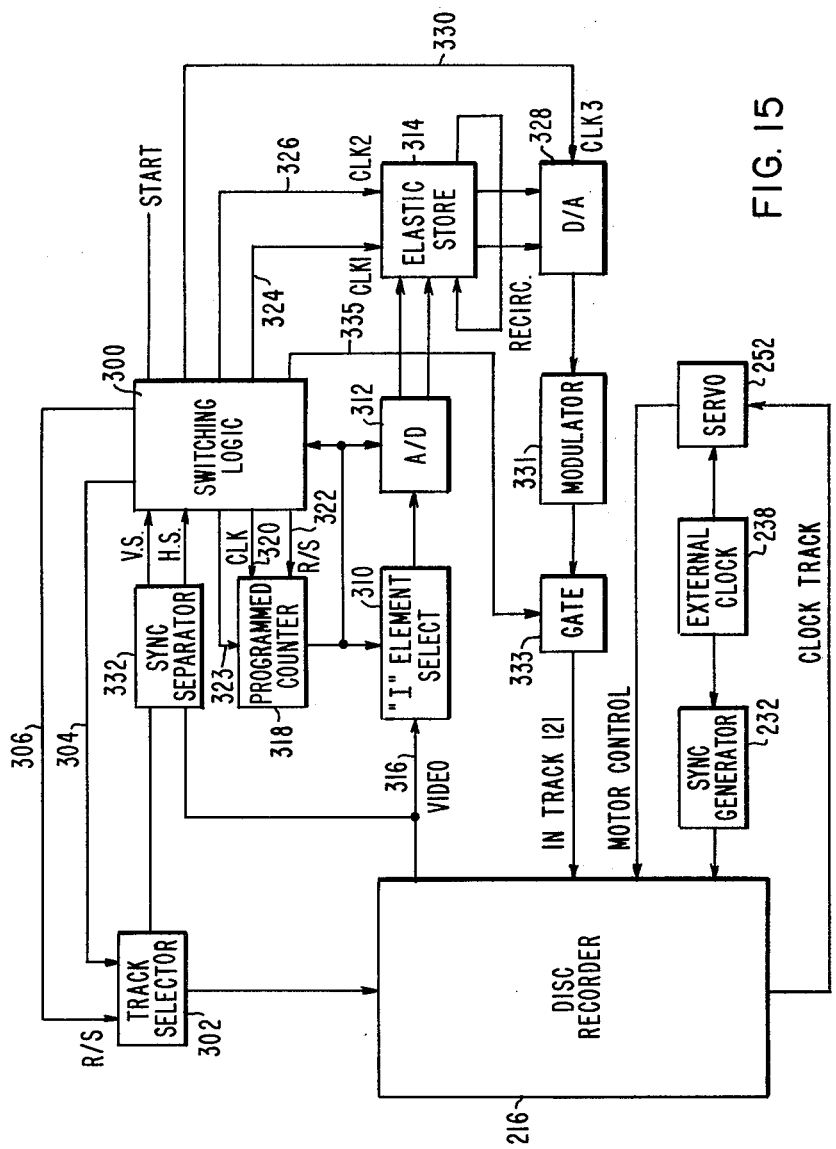
FIG. 15 is a block diagram illustrating how selected elements of the record on a video disc are recorded on an available track of the disc.
Figure 16:
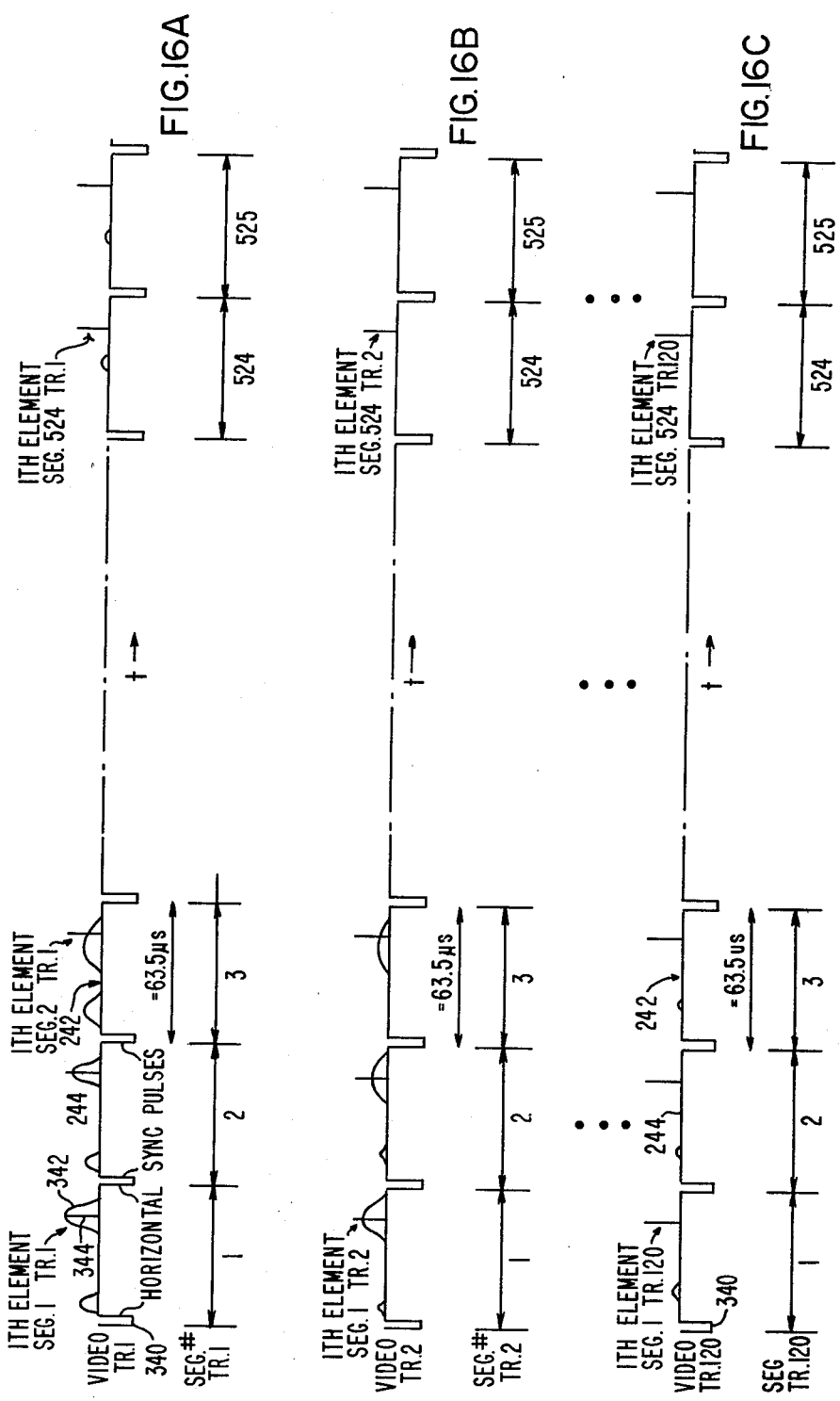
FIGS. 16A, 16B and 16C are graphs showing the relationship of a selected element on the tracks of a disc to the synchronizing pulses.

The apparatus for accomplishing this orthogonal transformation is shown in FIG. 15. The transformation process is illustrated in FIGS. 16A, 16B, 16C; 17; 18 graphs a, b, c, d; 19 graphs a, b, c; and 20A, 20B, 20C, 20D, and 20E.

The apparatus shown in FIG. 15 includes switching logic 300 and track selector 302. The track selector 302 is enabled by the switching logic 300 by an enabling signal along conductor 304 and reset by logic 300 by a signal along conductor 306. The track selector 302 when enabled acts on the disc recorder 216 (see also FIG. 9). It is assumed that records as disclosed above have been recorded in tracks 1 through 120 of the disc 240 (FIG. 11) in the disc recorder 216, and that the record as to the selected $i^{th}$ element of each of the segments 244 (FIG. 11) of each track 1 through 120 is to be recorded on track 121 (FIG. 17) of the same disc 240. Track 121 is provided with a record/playback head (not shown).

The apparatus shown in FIG. 15 also concludes an "i" element select 310, and A/D 312, and an elastic store 314. The A/D 312 and the elastic store 314 may be the A/D 188 and the elastic store 180 of the elastic store unit 26 (FIG. 5). The track selector 302 selects each track 1 through 120 in turn, and as each track is slected it transfers its intelligence for each segment 244 through conductor 316 to "i" element select 310. The selection of the $i^{th}$ (or $j^{th}$) element of each segment by the "i" element selector 310 is under control of a programmed counter 318 whose counting may be varied. The counting of the programmed counter 318 is set by clock signals supplied through conductor 320 from switching logic 300 and it is reset by reset signals supplied through conductor 322. The programmed counter is enabled to count by a signal from the switching logic along conductor 323. The programmed counter 318 also enables the A/D 312 and sends intelligence as to the counts back to switching logic 300. For each segment 244 of a track, the programmed counter enables the "i" element select 310 and the A/D 312 when it counts to the ith (or $j^{th}$) number and the intelligence of the $i^{th}$ (or $j^{th}$) element is converted by the A/D 312 and transmitted to the elastic store 314. Typically 525 such $i^{th}$ or $j^{th}$ elements are selected for each segment of track 121. The recording of magnitudes in the elastic store 314 is timed by clock signals along conductors 324 from the switching logic 300. Clock signals along conductor 324 time the transfer of the $i^{th}$ signal intelligence from each track. The apparatus includes a D/A 328 which is timed by clock signals along conductor 330 from switching logic. When the elastic store stores the data of the $i^{th}$ element from the segments of each track in its turn, the D/A 328 is enabled by CLK 2 on line 326 to convert the magnitudes in the elastic store and the analog intelligence is then recorded in a segment 244 on the 121st track (FIG. 17) of the disc 240. Each segment 244 corresponds to a line on the CRT. The D/A 328 is connected to the disc recorder 216 through a modulator 331 and a gate 333 analogous to the modulator 235 and the gate 234 of the disc recorder (FIG. 9). To record the intelligence in the elastic store 314 the gate 333 is opened by a signal from the switching logic 300 along conductor 335 and the signals converted by the D/A 328 to analog signals and M modulated by the modulator 331 are clocked in by clock 3 from the switching logic.

The apparatus also includes a sync separator 332 which receives the sync signals from the disc recorder, separates them into horizontal and vertical sync signals and supplies them to switching logic 300.

FIGS. 16A, 16B, and 16C show the manner in which the intelligence is selected from each track. The upper array of each set of FIGS. 16A, 16B and 16C represents a track 242 of the 120 tracks. FIG. 16A represents track 1; FIG. 16B, track 2; and FIG. 16C, track 120. The lower array shows the number of the segments 244; there are 525 segments corresponding to 525 CRT lines. At the start of each segment 244 there is a horizontal sync pulse 340. Within each segment 244 a line 344 is shown to indicate the position of the $i^{th}$ record. In some of the arrays a curve 342 is shown to indicate the magnitude of the $i^{th}$ record.

Figure 17:
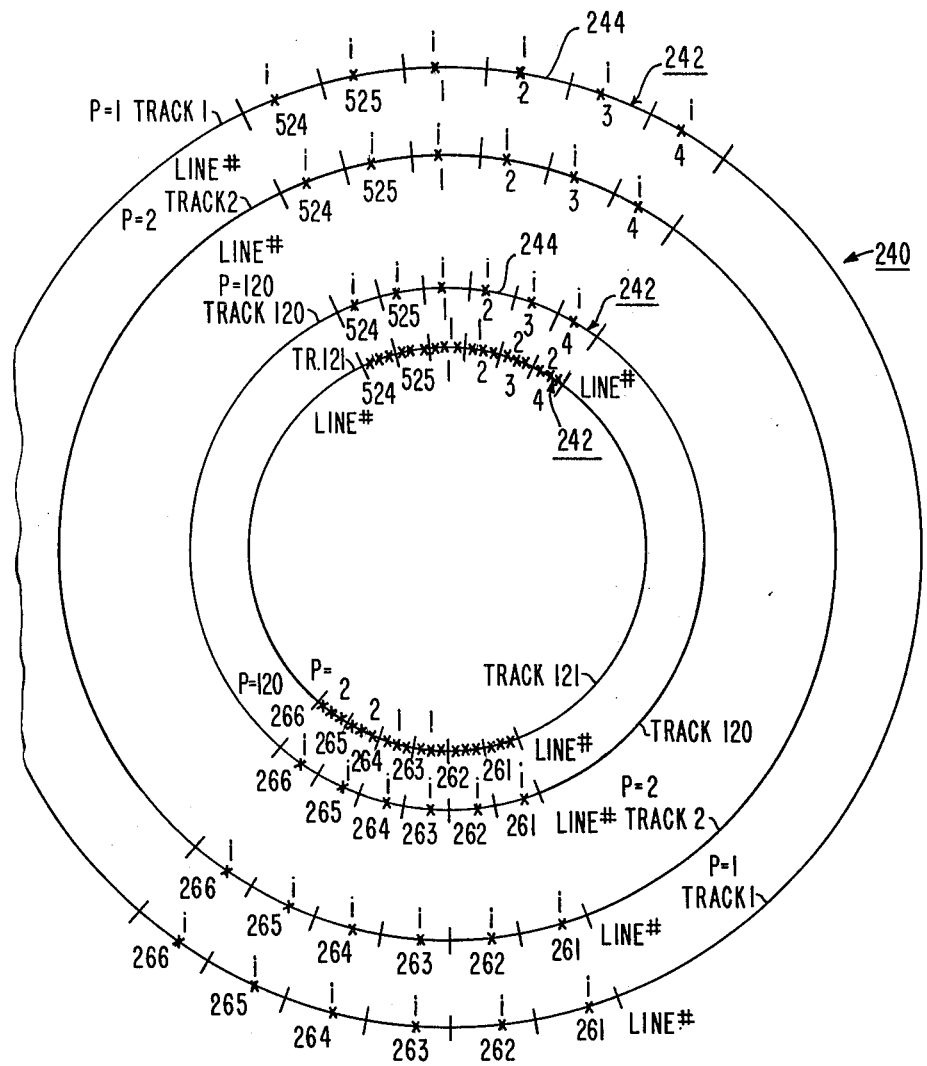
FIG. 17 is a diagram showing the manner in which selected elements recorded on tracks of a disc are recorded on an available track of the disc.

FIG. 17 shows a video disc 240 with several tracks 242 representing 120 tracks. The tracks are labeled track 1, track 2 and track 120 to correspond to FIGS. 16A, 16B and 16C. The segments 244 of each track are separated by radial lines and numbered 1, 2, 3, etc., to 525. The position of the $i^{th}$ record in each track is represented by an X. In track 121 the record for the $i^{th}$ element in each of the segments 244 of the 120 tracks 242 is recorded. It is stated above that the same intelligence is recorded in each pair of successive segments and each pair of the complementary segments whose intelligence is interlaced with the last-named pair. The same intelligence is then recorded in each track in segments 1, 2, 263 and 264, in segments 3, 4, 265, 266, etc. For proper display of the $i^{th}$ element of tracks 1 through 120 it is necessary that the pairs of segments 1, 2 and 263, 264 and 3, 4 and 265, 266, etc., of track 121 bear the same intelligence. It is for the reason that the segments of track 121 bear the same intelligence that these segments of track 121 are numbered 1, 1-2, 2, etc. It is to be noted that not only are the first and second segments numbered 1, 1 and the third and fourth numbered 2, 2, but the segments displaced 180° from these segments are similarly numbered. The 263rd and 264th segments are numbered 1, 1 and the 265th and 266th 2, 2.

Figure 18:
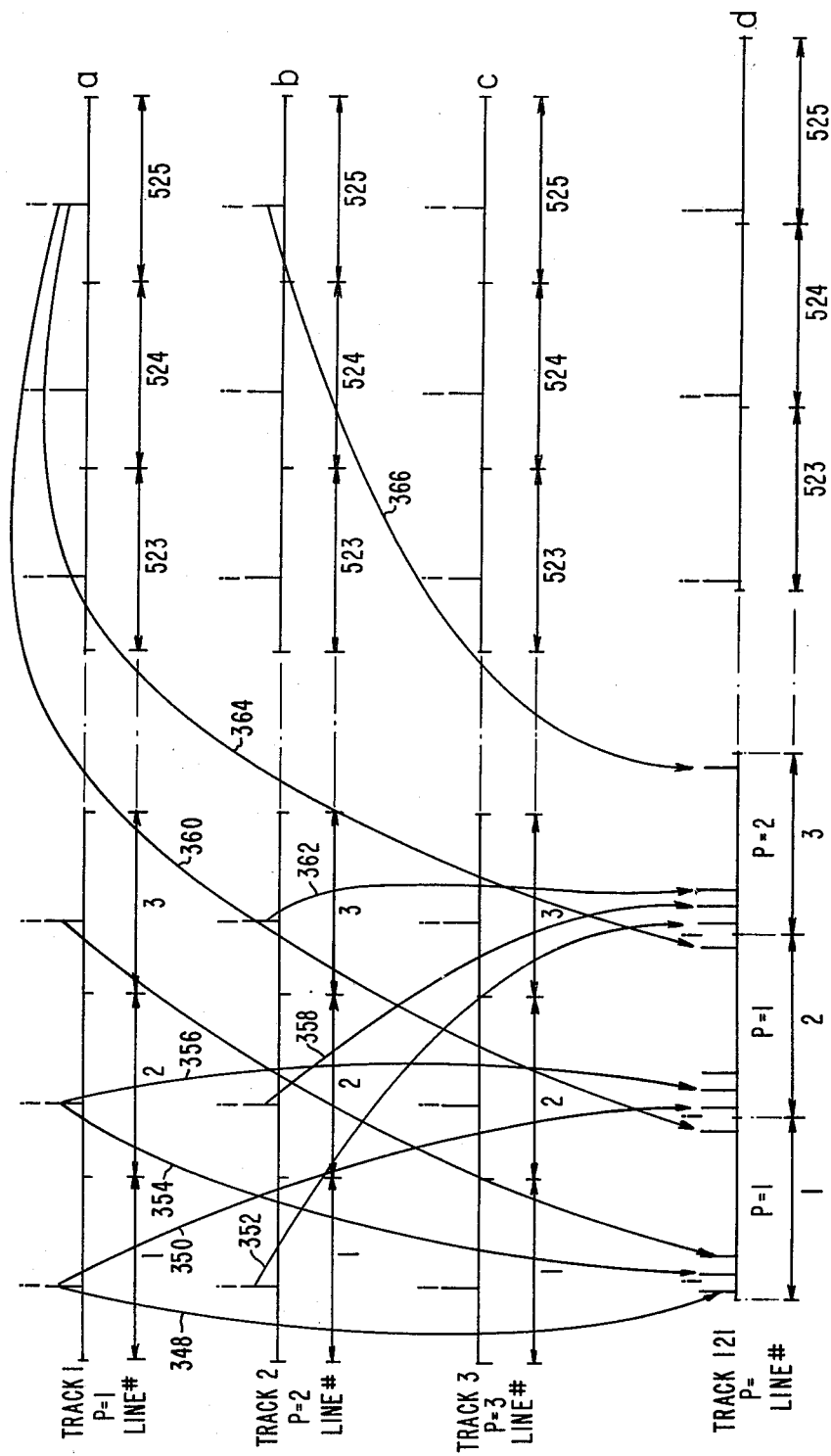
FIGS. 18 and 19 are diagrams which show the relationship between selected elements previously recorded on tracks a, b and c and a and b respectively on a disc and the corresponding elements recorded on the available empty track d and c respectively of the disc.
Figure 19:
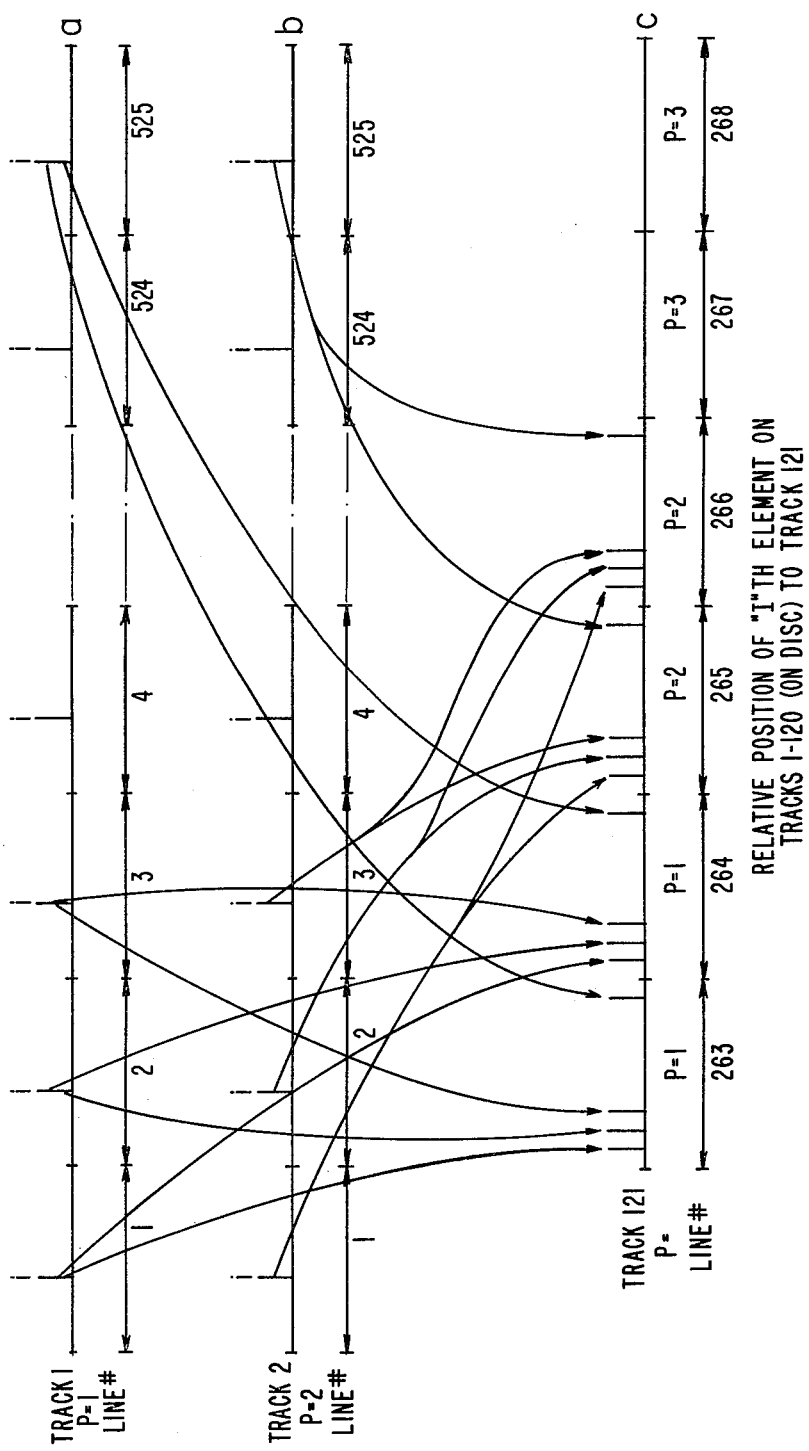

The manner in which intelligence from tracks 1 through 120 is recorded on track 121 as illustrated in FIGS. 18 and 19. Each of the arrays a, b, c, d of FIG. 18 represents sections of a track on record 240; a, b, c of FIG. 18 represent tracks 1, 2, 3 and d represents track 121. The tracks are labeled the same as in FIG. 17; the first three segments 1, 2, 3 and the last three segments 523, 524 and 525 are presented. The arrows 348 through 366 in FIG. 18 shows the transfer of recordings of the $i^{th}$ element from tracks 1 and 2 to track 121. Arrows 348 and 350 show that the $i^{th}$ element of segment 1 of track 1 is recorded both in the first and second segment of track 121. Arrows 354 and 356 show that the $i^{th}$ element of segment 2 of track 1 are recorded, as the second elements, of both the first and second segments of track 121. Arrows 352 and 358 show that the $i^{th}$ elements of segments 1 and 2 of track 2 are recorded as the first and second elements in the third segment of track 121. The same intelligence is recorded as the first and second elements in the fourth segment. Arrows 360 and 364 show that the $i^{th}$ element of segment 525 are recorded as the last elements of both the first and second segments of track 121. FIG. 19 shows a similar relationship for segments 263, 264, etc., of tracks 1 through 120 and track 121. To produce a track 121 as described, the magnitude must be stored in the elastic store 314 in the proper order. These magnitudes are selected by the "i" element select 310 in the order required.

FIG. 20A shows a work block W whose surface 370 is scanned by acoustic energy pulses. The positions of the acoustic-energy pulses are identified by coordinates S in depth, P vertically, and G horizontally. With the acoustic energy impinging on the surface 370 of the work, the pencils 45 (FIG. 2) produced by the propagation from the focused-arc transducer 37 are propagated along the S coordinate; the acoustic energy from the acoustic-lens transducer is also propagated along the S coordinate. The echo train from each pencil 45 is displayed as a line on the CRT and the echo trains from the line of pencils 45 in each SG plane at any level P are displayed as a complete picture. This display for P=1 is shown in FIG. 20B; for P=2 in in FIG. 20C; and for P=3 in FIG. 20D. There are typically 120 such pictures. It has been stated that the acoustic energy from the acoustic-lens transducer 35 is propagated alternately with each pencil 45 from the focused-arc transducer 37 in each elemental area 38. The echoes from each pulse from the acoustic-lens transducer is displayed as the last line of elements 372 or the last several elements of each picture.

As has been disclosed, the echo pattern in any selected PG plane may be presented for study by recording the intelligence for S=i for all pictures (120) on the 121st track of the disc 240 and reproducing the corresponding picture. When S−i=n, n being the last element of each row, in the SG plane, a holographic echo pattern is recorded in track 121 of the disc 240. This pattern may be reproduced on a film and reconstructed with a laser beam. This display is shown in FIG. 20E. Likewise an echo pattern in any selected SP plane may be reproduced as a picture by recording the intelligence for P=i on the 121st track of disc 240 and reproducing the record on a CRT.

Figure 21:
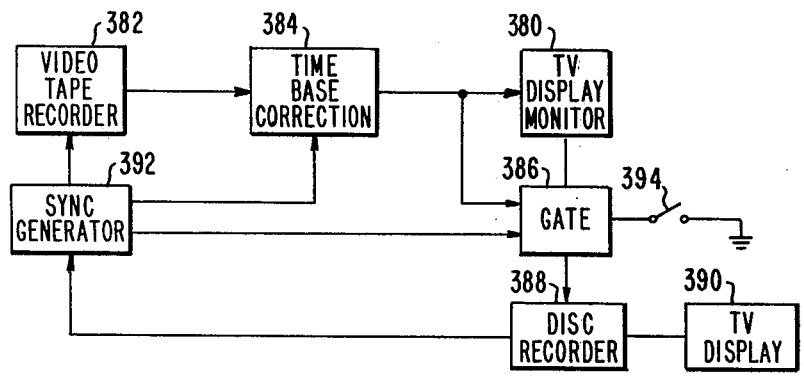
FIG. 21 is a block diagram showing how video tapes produced from the discs are displayed.

As has been stated, the record may be produced on a video tape which may be stored for future use. Typically, a number of sets of pictures, each set displaying an echo pattern from a region of work W of a suspected flaw, are stored on the magnetic tape, with each set separated from the other by a trailer (typically, 2 seconds) which contains synchronizing information. FIG. 21 shows a block diagram of playback apparatus for the video tape. This apparatus includes a TV display monitor 380 which receives the output of the video tape recorder 382 through a time base correction 384. The output of the video tape recorder is also supplied to a video disc record 388 through a gate 386. The output of the disc record 388 is displayed on TV display 390. There is a sync generator 392 which provides synchronizing signals to the disc record 388 through the gate 386 and to the video tape recording 382. The sync geneerator 392 supplies sync signals to the time base connection 384.

For study of a particular picture, the tape record 282 is run and its output video signal is displayed on the TV display monitor 380. Each picture, which represents one horizontal scan of the transducer subassembly 25, occupies 1/30 of a second of the display followed by the next picture representing the next horizontal scan. This continues for a period of several seconds until the total set (sonic scan of that location) is completed. Each sonic scan line is displayed as one picture. There are 120 sonic scan lines and therefore 120 pictures. Each picture is displayed for 1/30 second. Therefore to display 120 pictures or 120 sonic scan lines the time taken is 120×1/30=4 seconds. Following this there are sets of pictures of other locations. Identification of locations is made by words added to the audio track during the tape recording process, i.e., "location 1," "location 20," or by other coding techniques.

When the particular set of pictures is found, it is recorded on the disc recorder 388 for continuous "stop action" viewing on a TV display 390. Individual pictures can be studied by operation of the manual gate switch 394 which positions the replay head on successive tracks. This is accurately timed by "AND" gating (not shown) with the vertical synchronizing signal from the sync generator 392 to avoid "rolling" on the monitor 380.

Both the video tape recorder 382 and the disc motors (not shown) are servo controlled to the synchronizing signal from the sync generator 392. However, in the video tape recorder 382 in particular, it is difficult to accurately control fast variations of speed and this will result in timing variations in the replayed signal. This can be overcome by means of a time-base correction 384. With this arrangement the horizontal synchronizing signals recovered from the replayed video signals from the tape recorder are compared with the horizontal synchronizing signals from the crystal controlled synchronizing generator 392. Variations in speed are detected as phase and frequency variations and used to vary an electronically variable time delay (not shown) which is very fast acting; thus timing variations are virtually removed. Such a system is required for good quality slow motion replay of color sequences, but it is expected that perfectly adequate performance for the present application can be accomplished without the use of an expensive time-base corrector 384. This will be ensured by careful matching of the characteristics of monitors 380, tape-recorder 382, and disc servo performance.

While preferred practices of this invention have been disclosed herein, many modifications thereof are feasible. This invention is not to be restricted except insofar as is necessitated by the spirit of the prior art.

What is claimed is:

1. The method of detecting, characterizing and studying flaws in work with apparatus including an elastic store, the said method comprising scanning successive elemental areas of said work with acoustic energy, deriving an acoustical echo train, resulting from said scanning acoustic energy, from each said elemental area, successively storing in said elastic store a set of magnitudes corresponding to successive echo components of each said echo train, said components of said set being derived from reflections from successive depths of said work under said elemental area, producing, from the sets of magnitudes derived from echo trains resulting from the scanning acoustic energy impinging on a plurality of successive elemental areas of said work, and stored in said elastic store, a video record of said sets of magnitudes corresponding to the content of said echo trains, producing a display of the content of said record on a cathode-ray tube, and viewing said display to detect, characterize and study the flaws, it any, in said work.

2. The method of claim 1 wherein the apparatus includes a focused-arc transducer for scanning the work and the scanning acoustic energy is at each elemental area focused along a line penetrating along the depth of said work below said elemental area, the echo components of the echo train from successive depths below said elemental areas being derived from the focused acoustic energy along said line at each of said depths.

3. The method of claim 1 wherein the successive elemental areas along successive strips of the work are scanned by the acoustic energy and wherein in producing the display of the content of the video record, on a cathode-ray tube, a complete picture is produced on said tube from the echo trains resulting from the scanning acoustic energy scanning the elemental areas along each of said strips.

4. The method of claim 1 wherein successive elemental areas along successive strips of the work are scanned by the acoustic energy and, in producing the video record, a track on said record is produced for the echo trains resulting from the acoustic energy scanning successive elemental areas along each of said successive strips.

5. The method of claim 4 wherein in producing the display of the content of the video record on the cathode-ray tube, a complete picture is produced on said tube for each track of the record.

6. The method of claim 1 wherein successive elemental areas along successive strips of the work are scanned by the acoustic energy and wherein the sets of magnitudes of the echo components of the echo train, resulting from the acoustic energy impinging on a selected elemental area of each of the strips, are stored in the elastic store, wherein a video record is produced of said sets of magnitudes so stored in the elastic store, wherein a display is produced on a cathode-ray tube of the content of said video record, and wherein said display is viewed to detect, characterize and study the flaws in said work.

7. The method of claim 1 wherein successive elemental areas along successive strips of the work are scanned by the acoustic energy, and wherein the video record produced of the magnitudes of the components of the echo trains stored in the elastic store are, for each said strip, contained in a track of the video record, there being a plurality of tracks on said video record, a track on said video record for each strip; the said method including the step of producing an additional track containing a selected magnitude from each track of predetermined number of said plurality of tracks, producing a display of the content of said additional tracks, and viewing said last-named display to detect, characterize or study flaws in said work.

8. The method of claim 1 wherein the elastic store includes a shift register, the echoes from each elemental area being stored as words in succession in said register in the order in which they are received, the words from the earlier-received echoes being shifted along said register as words from later-received echoes are shifted into said register, the words from said echoes being shifted out of said register and into the video record in the said order in which they are received.

9. The method of claim 8 wherein the words in the shift register, as they are shifted out of the shift register and recorded in the video record, are also shifted back into the shift register so that they may be repeatedly recorded in different portions of the video record.

10. The method of claim 1 wherein the display in the cathode-ray tube conforms to conventional television standards and wherein the echo components are so recorded on the video record that the echo train from each elemental area is reproduced along a line of the cathode-ray tube, and the echo trains from a plurality of successive elemental areas are produced as a complete picture on said cathode-ray tube.

11. The method of detecting, characterizing and studying flaws in work with apparatus including focused-arc acoustic energy transducer means, an echo-ranging subassembly connected to said transfer means, when actuated, to energize said transducer means and to process echo trains resulting from the acoustic energy from said transducer means impinging on said work and received by said transducer means, point-focusing transducer means, a holographic echo processing subassembly connected to said point-focusing transducer means, when actuated, to energize said point-focusing transducer means and to process echoes resulting from the acoustic energy from said point-focusing transducer means impinging on said work and received by said point-focusing transducer means, and an elastic store;

the said method comprising scanning said work with said focused-arc transducer means and with said point-focusing transducer means, actuating alternately said echo-ranging subassembly and said holographic echo processing subassembly as said work is scanned to produce and process alternately, from each of successive elemental areas of said work, echo trains produced by said focused-arc transducer means and said echo-ranging subassembly and echoes produced by said point-focusing transducer means and said holographic echo-processing subassembly, storing in said elastic store a set of magnitudes for each of said elemental areas, each set including magnitudes of successive echo components of each of said echo trains and magnitudes of each of said echoes from the echo components of each said set being derived from reflections from successive depths of said work and said echoes being derived from reflections at predetermined depths of said work under each of said elemental areas, producing from the said sets of magnitudes received from the echo trains and succeeding echoes resulting from the acoustic energy impinging on a plurality of elemental areas and stored in said elastic store, a video record of said sets of magnitudes, producing a display on a cathode-ray tube of the portion of the content of said video record corresponding to said echo trains, producing a hologram of the content of said video record corresponding to said echoes, viewing said display, and reconstructing and viewing said hologram to detect, characterize or study the flaws, if any, in said work.

12. The method of claim 11 including the steps of scanning successive strips of said work, with the focused-arc transducer means and said point-focusing transducer means storing in the elastic store, for each strip, separate sets of magnitudes, each set including magnitudes for each elemental area of said last-stored strip of successive echo components of each of the echo trains and elemental magnitudes of the echoes derived from said last-named elemental area, producing from the records in said elastic store, on each of a plurality of separate tracks of a video disc, a record of the sets of magnitudes derived from the echo trains and succeeding echoes resulting from the acoustic energy impinging on the elemental areas of a corresponding strip of each said strips, deriving from a set of magnitudes from the records on said plurality of separate tracks by selecting from each of said plurality of tracks the magnitudes of the echoes resulting from the acoustic energy from the point-focusing transducer means impinging on the work along each of said strips, and recording the selected magnitudes on another track of said video disc, producing a hologram of the magnitudes contained in said other track, and reconstructing and viewing said hologram to detect, characterize or study flaws in said work.

13. The method of claim 11 wherein successive strips of said work are scanned by said focused-arc transducer means and by said point-focusing transducer means, the said method including the steps of scanning successive strips of said work, each strip including successive elemental areas storing in said elastic store, for each strip, separate sets of magnitudes, each set including magnitudes of successive echo components of each of the echo trains and a magnitude corresponding to the echoes from each elemental area of the strip, producing from the records stored in said elastic store, on each of a plurality of separate tracks of a video record, a record of the sets of magnitudes derived from the echo trains and succeeding echoes resulting from the acoustic energy impinging on the elemental areas of each strip, deriving a new set of magnitudes from the records on said plurality of separate tracks by selecting from each of the records in said plurality of tracks, the magnitudes of the echo components resulting from the acoustic energy from the focused-arc transducer means impinging at a selected elemental area of each strip of the work, and recording the selected magnitudes on another track, displaying on a cathode-ray tube the record of said other track, and viewing said display to detect, characterize or study flaws in said work.

14. The method of claim 11 wherein each, the echo-ranging subassembly and the holographic echo-processing subassembly, is actuated at least a predetermined time interval after the actuation of the roller has terminated, said time interval being at least sufficient to afford the acoustic energy injected in the work by the other subassembly time to decay to a low magnitude.

15. The method of claim 11 wherein the holographic echo-processing subassembly is actuated a predetermined time interval after the actuation of the echo-ranging subassembly is terminated, said interval being sufficient just to afford the acoustic energy injected in the work by said echo-ranging subassembly time to decay to a low magnitude.

* * * * *